United States Patent
Kim

(10) Patent No.: US 11,487,352 B2
(45) Date of Patent: Nov. 1, 2022

(54) BIOMETRIC SENSOR MODULE AND ELECTRONIC DEVICE INCLUDING THE SAME

(71) Applicant: Samsung Electronics Co., Ltd., Suwon-si (KR)

(72) Inventor: Jinho Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 284 days.

(21) Appl. No.: 16/692,917

(22) Filed: Nov. 22, 2019

(65) Prior Publication Data

US 2020/0166992 A1 May 28, 2020

(30) Foreign Application Priority Data

Nov. 26, 2018 (KR) ........................ 10-2018-0147653

(51) Int. Cl.
*G06F 3/01* (2006.01)
*G06F 1/16* (2006.01)
(Continued)

(52) U.S. Cl.
CPC .......... *G06F 3/011* (2013.01); *A61B 5/02438* (2013.01); *A61B 5/681* (2013.01);
(Continued)

(58) Field of Classification Search
CPC ..... G06F 3/011; G06F 1/163; A61B 5/02438; A61B 5/681; A61B 2562/0233;
(Continued)

(56) References Cited

U.S. PATENT DOCUMENTS

2008/0093530 A1  4/2008  Hoelen et al.
2009/0162015 A1*  6/2009  Meir ..................... G02B 6/008
                                                         385/49
(Continued)

FOREIGN PATENT DOCUMENTS

JP      2013063203 A      4/2013
JP      2018-000541 A     1/2018
(Continued)

OTHER PUBLICATIONS

International Search Report and Written Opinion of the International Searching Authority in connection with International Application No. PCT/KR2019/015314 dated Feb. 20, 2020, 9 pages.
(Continued)

*Primary Examiner* — Omar Casillashernandez

(57) ABSTRACT

An electronic device includes: a housing including a front plate oriented in a first direction and a rear plate oriented in a second direction; a display visible through at least a portion of the front plate; and a biometric sensor module located between the front plate and the rear plate. The biometric sensor module may include: a cover glass oriented in the second direction; at least one light source configured to emit light to the outside; a light detector disposed adjacent to the at least one light source, and configured to receive reflected light corresponding to light emitted from the light source; a light guide disposed between the light detector and the cover glass, and configured to provide a path of the reflected light received by the light detector; and a circuit board electrically connected to the at least one light source and the light detector.

14 Claims, 12 Drawing Sheets

(51) Int. Cl.
*A61B 5/024* (2006.01)
*A61B 5/00* (2006.01)
*G06V 40/13* (2022.01)

(52) U.S. Cl.
CPC .......... *G06F 1/163* (2013.01); *G06V 40/1324* (2022.01); *A61B 2562/0233* (2013.01)

(58) Field of Classification Search
CPC ..... A61B 5/6802; A61B 5/0059; A61B 5/024; A61B 5/0261; A61B 5/7225; A61B 5/7235; A61B 5/7275; A61B 5/743; G06K 9/00046; G06K 9/0051; G06K 2009/00939; G06K 9/00885; G02B 6/0088
USPC ..................................................... 340/539.12
See application file for complete search history.

(56) References Cited

U.S. PATENT DOCUMENTS

| | | |
|---|---|---|
| 2011/0065482 A1 | 3/2011 | Koide et al. |
| 2014/0078359 A1 | 3/2014 | Lenchenkov et al. |
| 2016/0120421 A1 | 5/2016 | Matsuo |
| 2016/0278645 A1 | 9/2016 | Yoon |
| 2017/0055907 A1 | 3/2017 | Altebaeumer et al. |
| 2017/0118551 A1* | 4/2017 | Wagner ................ A61B 5/6802 |
| 2018/0000362 A1* | 1/2018 | Matsuo ................ A61B 5/7455 |
| 2018/0027931 A1 | 2/2018 | Baranski et al. |
| 2018/0116532 A1 | 5/2018 | Han et al. |
| 2018/0143368 A1 | 5/2018 | Hikmet et al. |
| 2018/0295222 A1 | 10/2018 | Jung et al. |
| 2018/0353134 A1* | 12/2018 | Walter ................ A61B 5/6843 |
| 2020/0046235 A1 | 2/2020 | Jung et al. |

FOREIGN PATENT DOCUMENTS

| | | |
|---|---|---|
| KR | 20110007412 A | 1/2011 |
| KR | 10-2018-0082738 A | 7/2018 |
| KR | 10-2018-0093628 A | 8/2018 |

OTHER PUBLICATIONS

Supplementary European Search Report dated Nov. 11, 2021 in connection with European Patent Application No. 19 88 9494, 10 pages.

* cited by examiner

BIOMETRIC SENSOR MODULE AND ELECTRONIC DEVICE INCLUDING THE SAME

CROSS-REFERENCE TO RELATED APPLICATIONS

This application is based on and claims priority under 35 U.S.C. 119 to Korean Patent Application No. 10-2018-0147653, filed on Nov. 26, 2018, in the Korean Intellectual Property Office, the disclosure of which is herein incorporated by reference in its entirety.

BACKGROUND

1. Field

Various embodiments relate to an electronic device, and more particularly, to an electronic device including a biometric sensor.

2. Description of Related Art

The term "electronic device" may mean a device that performs a specific function depending on a programs incorporated therein, such as an electronic scheduler, a portable multimedia reproducer, a mobile communication terminal, a tablet PC, an image/sound device, a desktop PC, a laptop PC, or a vehicular navigation system, as well as a home appliance. The above-mentioned electronic devices may output, for example, information stored therein as sound or an image. As the integration degree of electronic devices has increased and super-high speed and large-capacity wireless communication have become popular, various functions have recently been provided in a single electronic device, such as a mobile communication terminal. For example, various functions, such as an entertainment function (e.g., a game function), a multimedia function (e.g., a music/video reproducing function), a communication and security function for mobile banking, a schedule management function, and an e-wallet function, are integrated in a single electronic device, in addition to a communication function.

Portable electronic devices are generally equipped with a flat type display and a battery, and are classified into a bar-type, a folder-type, and a sliding-type based on the external appearances thereof. Recently, as the electronic communication technology has been advanced, electronic devices have been miniaturized, and as a result, electronic devices, which are wearable on a portion of a human body, such as a wrist or a head, have become commercially available. In recent years, starting with mobile communication terminals, wearable electronic devices, which are worn on a human body, have been added to electronic devices. The electronic devices have been gradually reduced in weight, thickness, length, and size, and have been provided with various functions so as to satisfy consumers' desires.

Various functions provided by electronic devices include functions that are executed using sensors. The sensors may collect information related to an electronic device, outside of the electronic device, or a user. An electronic device may include one or more sensors, and various services may be provided using the information collected through various sensors.

SUMMARY

Generally, a biometric sensor module mounted in an electronic device may include a light source and a light detector. The light emitted through the light source reaches the user's body, and biometric information acquired through a predetermined signal may be transmitted to the light detector. In this case, when noise is transmitted to the light detector in addition to a signal related to the biometric information, it is impossible to acquire accurate biometric information. Main noise includes crosstalk noise occurring when light emitted from the light source does not enter the user's skin and is detected by the light detector, and stray light noise (background noise) occurring when the light detector does not detect light emitted from the light source but detects external light in the case in which the biometric sensor module and the user's skin are not in close contact with each other.

According to an embodiment, a light guide may be disposed on a light path of the biometric sensor module so that noise other than a signal related to a living body is not detected by the light detector.

According to an embodiment, the light guide is disposed on the light path of the light source to improve the rectilinear advancement property of light in the traveling direction, thereby reducing a noise effect.

An electronic device according to various embodiments may include: a housing including a front plate oriented in a first direction and a rear plate oriented in a second direction, which is opposite the first direction; a display visible through at least a portion of the front plate; and a biometric sensor module located between the front plate and the rear plate, the biometric sensor module being exposed through at least a portion of the rear plate. The biometric sensor module may include: a cover glass oriented in the second direction; at least one light source configured to emit light to the outside; a light detector disposed to adjacent to the at least one light source, and configured to receive reflected light corresponding to light emitted from the light source; a light guide disposed between the light detector and the cover glass, and configured to provide a path of the reflected light received by the light detector; and a circuit board electrically connected to the at least one light source and the light detector.

A biometric sensor module according to various embodiments may include: a cover glass exposed to the outside; at least one light source configured to emit light to the outside; a light detector disposed to adjacent to the at least one light source, and configured to receive reflected light corresponding to light emitted from the light source; a first light guide disposed between the light source and the cover glass, and configured to provide a path of the light emitted from the light source; a second light guide disposed between the light detector and the cover glass, and configured to provide a path of the reflected light received by the light detector; and a circuit board electrically connected to the at least one light source and the light detector.

An electronic device according to various embodiments may include: a housing including a front plate oriented in a first direction and a rear plate oriented in a second direction, which is opposite the first direction; a display visible through at least a portion of the front plate; and a biometric sensor module located between the front plate and the rear plate, the biometric sensor module being exposed through at least a portion of the rear plate. The biometric sensor module may include: a cover glass oriented in the second direction; at least one light source configured to emit light to the outside; a light detector disposed to adjacent to the at least one light source, and configured to receive reflected light corresponding to light emitted from the light source; a light guide disposed between the light source and the cover glass, and configured to provide a predetermined path of the light emitted from the light source; and a circuit board electrically connected to the at least one light source and the light detector.

An electronic device according to an embodiment is capable of preventing crosstalk noise from being detected by the light detector by a light guide disposed on a light path of the biometric sensor module. Accordingly, it is possible to acquire noiseless biometric information of the user.

An electronic device according to an embodiment is capable of preventing stray light noise from being detected by the light detector by a light guide disposed on a light path of the biometric sensor module. Accordingly, since an additional processing operation for removing the stray light noise is omitted, it is possible to improve the processing rate and energy efficiency of the sensor module.

With the electronic device according to an embodiment, since the light guide is disposed on the light path of the light source, it is possible to improve the rectilinear advancement property of light in the traveling direction, thereby reducing a noise effect.

According to various embodiments, it is possible to provide an electronic device having an appearance that is able to implement comfortable wearability on a human body and smooth function.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

The above and other aspects, features, and advantages of the disclosure will be more apparent from the following detailed description taken in conjunction with the accompanying drawings, in which.

DETAILED DESCRIPTION

FIGS. 1 through 15, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Figure 1:
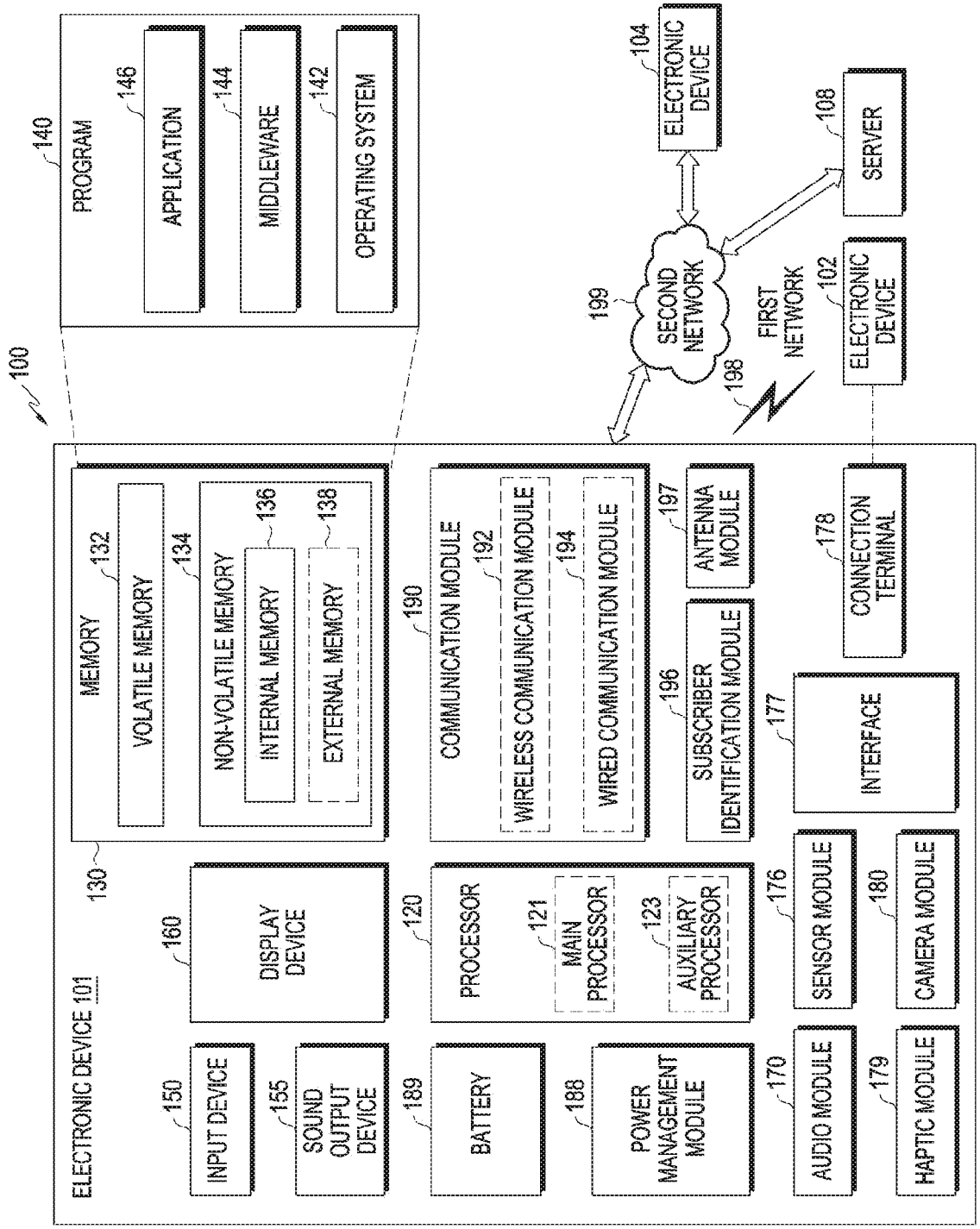
FIG. 1 illustrates a block diagram of an electronic device according to various embodiments in a network environment.

FIG. 1 illustrates a block diagram of an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing recordings, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wired) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wired) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his or her tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., PCB). According to an embodiment, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wired), wirelessly, or via a third element.

As used herein, the term "module" may include a unit implemented in hardware, software, or firmware, and may interchangeably be used with other terms, for example, "logic," "logic block." "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
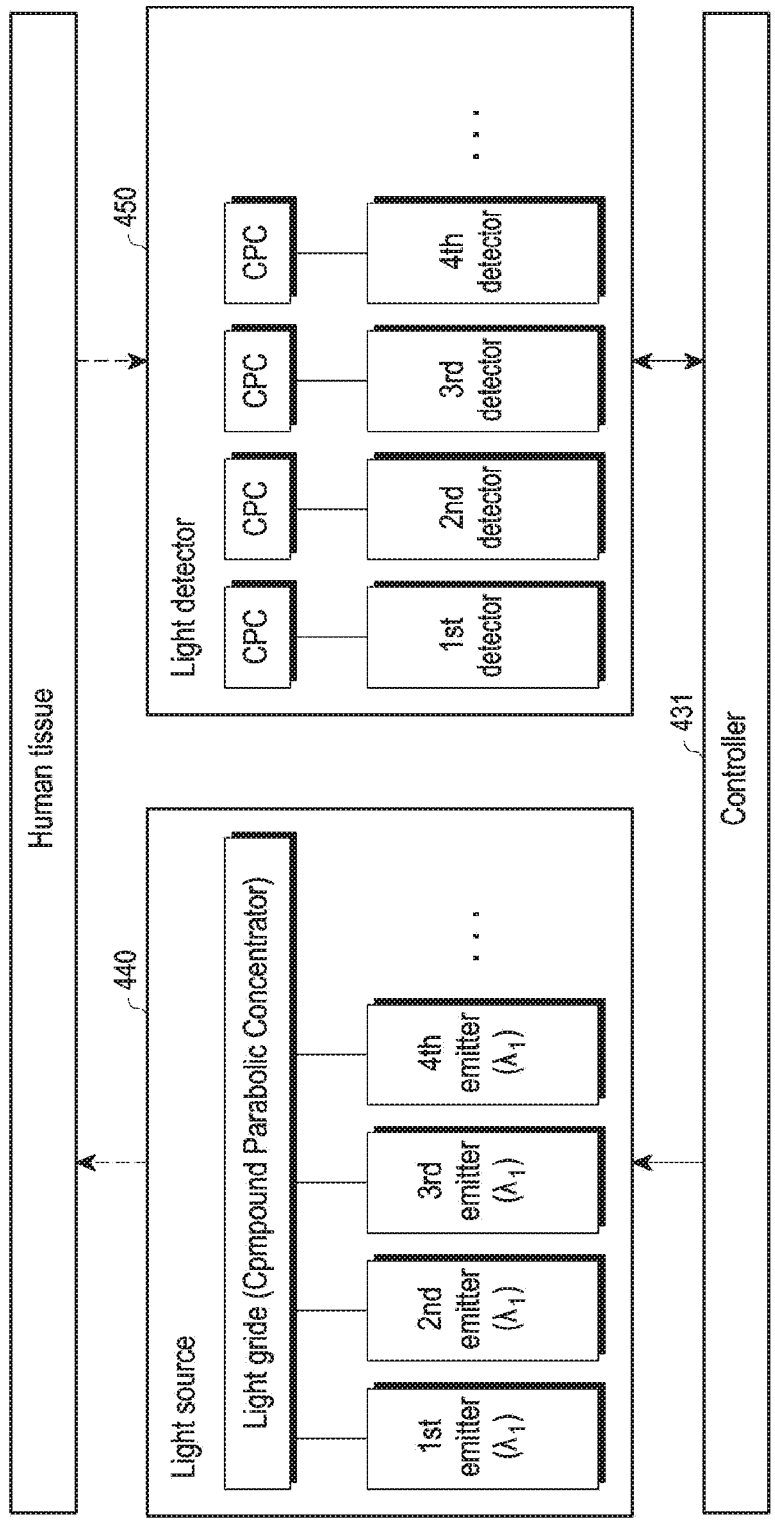
FIG. 2 illustrates a block diagram representing the association relationship between a biometric sensor module in an electronic device and a user's body according to various embodiments.

FIG. 2 illustrates a block diagram representing the association relationship between a biometric sensor module in an electronic device and a user's body according to various embodiments.

Referring to FIG. 2, an electronic device may include a light source (emitter) 440, a light detector (or sensor) 450, and a controller 431 for controlling the light source and the light detector.

According to various embodiments, the controller 431 may provide an electrical signal to control the operations of the light source 440 and the light detector 450, and may receive a signal received by the light detector 450. The controller 431 may be connected to a processor (e.g., the processor 120 of FIG. 1) to control the intensity, driving channel, driving period, or the like of the light source 440.

According to various embodiments, each or one of the light source 440 and the light detector 450 may include a light guide (e.g., a compound parabolic collector (CPC) structure). The light guide may be disposed on the path of the light generated by the light source 440 or the light incident on the light detector 450 so as to deform each of the lights (e.g., directional filtering) and to guide each of the lights in the form of an optical signal (broken arrow) to interact with the skin.

According to various embodiments, the light source 440 may be configured to emit one wavelength or two or more wavelengths. The light source 440 may include one or more light emitting diodes (LEDs) or laser diodes (LDs), and respective LEDs and LDs may have different wavelengths. As another example, the light source 440 may have an array in which several LEDs having the same wavelength are arrayed.

According to various embodiments, at least one light detector 450 may be provided, and may receive light reflected by an object (e.g., the user's body) after being emitted from the light source 440. For example, the light detector 450 may detect light reflected or transmitted through a blood vessel in the skin. As another example, the light detector 450 may determine the presence or absence of an object or may image the shape of the object. The light detector may be a photodiode or an image sensor.

According to various embodiments, the processor 120 may control a sensor module including the light source 440 and the light detector 450. For example, in the case of a sensor having a plurality of LEDs, it is possible to select an LED to be activated depending on the type or service of biometric measurement. As another example, a heart rate may be measured using a green LED and a red/IR LED may be activated for SpO2 measurement. As another example, the intensity of the LED may be adjusted, or the gain of the light detector may be controlled depending on the color of the skin. As another example, a measurement cycle may be adjusted to, for example, once per 1 minute, once per 1 hour, or the like depending on the service, and detailed operations, such as monitoring for 10 sec and monitoring for 20 sec in one measurement session, may be controlled. Such operations may vary depending on the battery size, the power efficiency, the consumed current of the sensor, the use purpose, and the type of the electronic device.

Figures 3A, 3B:
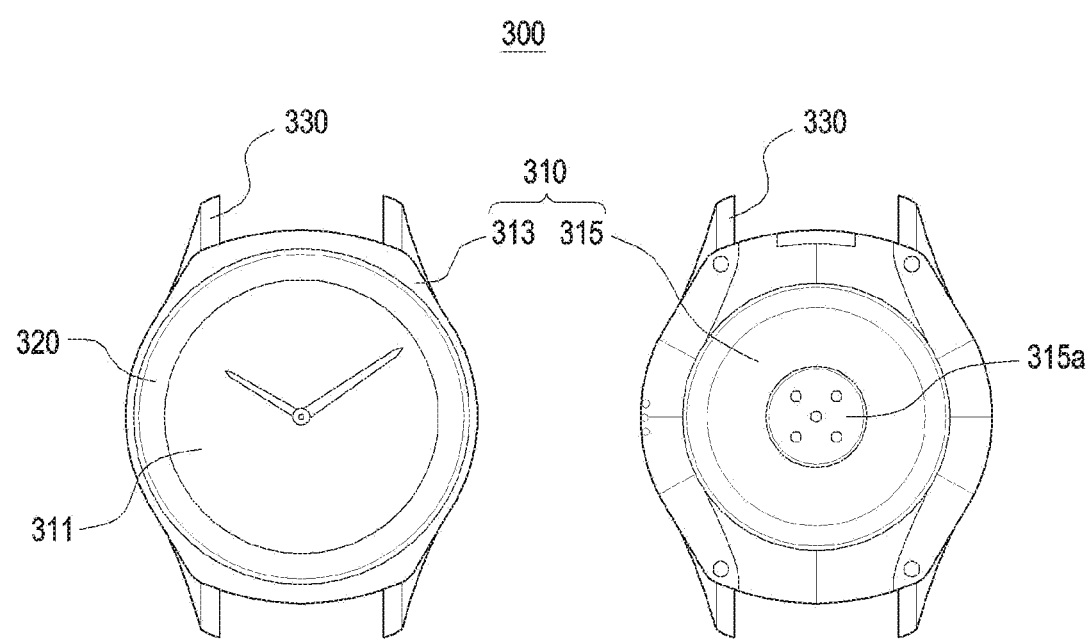
FIG. 3A illustrates a front view of an electronic device according to one of various embodiments.
FIG. 3B illustrates a rear view of the electronic device according to one of various embodiments, in which the electronic device is viewed from another direction.

FIG. 3A illustrates a front view of an electronic device according to one of various embodiments. FIG. 3B illustrates a rear view of the electronic device according to one of various embodiments, in which the electronic device is viewed from another direction.

An electronic device according to various embodiments may be a portable electronic device, such as a mobile communication terminal, or a wearable electronic device that is wearable on the user's body. An electronic device according to various embodiments will be described with reference to a smart watch as an example.

Referring to FIGS. 3A and 3B, an electronic device 300 according to various embodiments includes a housing 310 including a transparent plate 311, a bezel 320, and detachable portions 330. The term "first direction" used for describing various embodiments mean a direction perpendicular to one face of the transparent plate 311, and the term "second direction" may mean a direction opposite the "first direction".

According to various embodiments, the housing 310 may include a first face 313 oriented in the first direction and a second face 315 oriented in the second direction that is opposite the first direction. The front face of the housing 100 is configured to be openable, and the transparent plate 311 may be mounted to form at least a portion of the first face 313 corresponding to the front face of the housing 310 so as to close the opened first face 313 of the housing 310. The first face 313 and the second face 315 may each have a plate shape, and may have each a curved face in the edge portion thereof. The second face 315 of the housing 310 may include at least one transparent area 315a such that light generated in an optical element (e.g., the light source and/or light detector) disposed inside the housing is emitted to the outside.

According to various embodiments, various circuit devices, such as a processor 120 (e.g., an application processor (AP) described above with reference to FIG. 1), memory 130, an input/output interface 150, and a communication interface 170, may be accommodated in the housing 310, and power may be secured by accommodating a battery (not illustrated) in the housing 310.

According to various embodiments, the housing 310 may be made of a metal material. According to various embodiments, a portion (e.g., the periphery) of the housing 310 may be made of a metal material, and the remaining portion of the housing 310 may be made of a plastic material.

According to various embodiments, the transparent plate 311 may be disposed on the first face 313 of the housing 310. The transparent plate 311 may be made of a transparent material, such as glass or a resin (e.g., acrylic or polycarbonate) so as to implement a screen output from a display (e.g., the display 160 of FIG. 1). For example, a screen in the form of an analog watch may be output to the transparent plate 311.

According to various embodiments, the bezel 320 may be disposed in the periphery of the transparent plate 311. The bezel 320 may be relatively rotatably coupled with the housing 310 to rotate along the periphery of the transparent plate 311. The bezel 320 may be made of a metal material so as to achieve a beautiful appearance of the electronic device 300. According to an embodiment, when the bezel 320 is made of a metal material, the bezel 320 may be utilized as an antenna radiator.

According to various embodiments, the detachable portions 330 may be disposed to extend and protrude from the opposite ends of the housing 310 in directions away from each other. The detachable portions 330 may be coupled with wearing units (not illustrated) arranged to be worn on the user's wrist. The detachable portions 330 are formed with fastening grooves to which the wearing units are engaged, respectively. A plurality of fastening grooves may be formed on the side surface of the housing 310, or a fastening groove may have a closed curve shape extending along the periphery of the housing 310. The wearing units may be configured in various types using various materials (e.g., rubber, plastic, and metal). Since the various types of wearing units may be attached to/detached from the detachable portions 330 of the electronic device 300 according to the preference of the user, so that it is possible to make the appearance of the electronic device beautiful.

Figure 4:
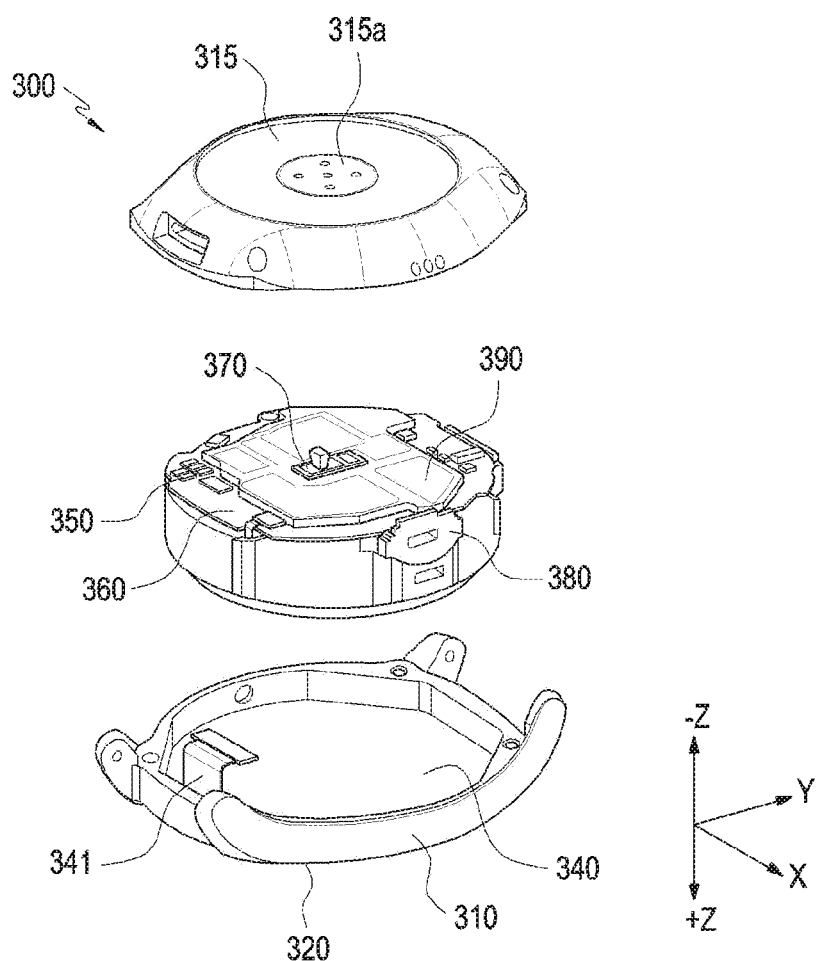
FIG. 4 illustrates an exploded perspective view of the internal structure of an electronic device according to one of various embodiments.

FIG. 4 illustrates an exploded perspective view of the internal structure of an electronic device according to one of various embodiments.

In FIG. 4, in an orthogonal coordinate system of three axes, the "X axis" may correspond to the width direction of the electronic device 300, the "Y axis" may correspond to the length direction of the electronic device 300, and the "Z axis" may correspond to the thickness direction of the electronic device 300.

Referring to FIG. 4, according to one of various embodiments, the electronic device 300 may include a housing 310, a bezel 320, a display 340, an electronic component 350, a main circuit board 360, a bracket 380, a battery, and a biometric sensor 370. The structure of the housing 310 and/or the bezel 320 of the electronic device 300 illustrated in FIG. 4 may correspond to the structure of the housing 310 and/or the bezel 320 illustrated in FIGS. 3A and 3B.

According to various embodiments, the housing 310 may receive various electronic components including, for example, the display 340, the main circuit board 360, the electronic component 350, and/or the biometric sensor 370. A portion of the housing 310, for example, the side face of the housing 310, may be at least partially made of a material that transmits a wireless signal or a magnetic field.

According to various embodiments, the display 340 may be coupled in a second direction (−Z) of the transparent plate (the transparent plate 311 in FIG. 3A). The display 340 may display image information (e.g., a photograph or a video image) to the outside through the transparent plate 311, and may output an execution screen for various applications (e.g., a game, internet banking, and schedule management) in response to the user's operation.

According to various embodiments, the display 340 may include a liquid crystal display (LCD), a light-emitting diode (LED) display, an organic light-emitting diode (OLED) display, a microelectromechanical system (MEMS) display, or an electronic paper display. The display 340 may include a touch screen panel integrated therewith to perform a touch screen function. According to various embodiments, the display 340 may have an antenna radiator mounted on the inner or outer face thereof to perform a wireless communication function.

According to various embodiments, the display 340 may be electrically connected to the display circuit board 341, and the display circuit board 341 may be disposed inside the housing 310. The display circuit board 341 may transmit an electrical signal for driving the display 340.

According to various embodiments, the main circuit board 360 may be disposed to face a battery (not illustrated). On the main circuit board 360, a processor, a communication module, or the like may be mounted in the form of an integrated circuit chip. The main circuit board 360 may be electrically connected to the battery. According to various embodiments, the main circuit board 360 may be electrically connected to an electronic component 350 including the antenna radiator or the like through a connector.

According to various embodiments, the electronic component 350 may be disposed on the main circuit board 360, and may include an antenna radiator and/or a wireless charging antenna. According to an exemplary embodiment, the antenna radiator may transmit and receive a wireless signal in a Magnetic Security Transmission (MST) manner. For example, the antenna radiator may be an MST antenna. As another example, the antenna radiator may be a Near-Field Communication (NFC) antenna that transmits/receives a wireless signal in an NFC manner. A shielding structure may be disposed around the antenna radiator so as to prevent signal interference between the antenna radiator and other electronic components, such as a sensor module.

According to an embodiment, the wireless charging antenna may be attached to one face of the main circuit board 360. The wireless charging antenna may be in the form of a flat coil. The wireless charging antenna may be made of a conductive material, and may be electrically connected to the main circuit board 360. The wireless charging antenna may generate current by electromagnetic induction generated from an external electronic device. The current generated in the wireless charging antenna is able to charge the battery (not illustrated) through the main circuit board 360.

According to various embodiments, a heat dissipation structure (not illustrated) may be provided between the main circuit board 360 and the battery. For example, the heat dissipation structure may receive heat generated from the main circuit board 360, thereby preventing the main circuit board 360 from being overheated. According to various embodiments, a shielding structure 390 may be disposed between the main circuit board 360 and the second side 315. The shielding structure 390 may shield a space between the electronic components on the main circuit board 360 and the biometric sensor 370 in order to prevent mutual interference therebetween.

According to various embodiments, the second face 315 formed in the second direction (−Z axis direction) on the housing 310 may form a rear cover of the housing 310. The rear cover may be made of a glass material. The rear cover may come into contact with a part of a human body (e.g., a wrist). According to various embodiments, the rear cover may be made of a transparent material, such as transparent reinforced plastic, without being limited to the glass material. The center area of the rear cover may be made of a transparent plate for a sensing operation of the biometric sensor 370, and the other area may be formed of an opaque plate. The rear cover may include at least one transparent area 315*a* such that light generated from an internal optical element may be emitted to the outside.

According to various embodiments, the biometric sensor 370 may be disposed between the main circuit board 360 and the second face 315 to sense the user's biometric information. For example, the biometric sensor 370 may include a heart rate monitor (HRM). Based on the reflection of light depending on a change in a blood volume in a blood vessel of the skin, the biometric sensor 370 may detect the contraction/expansion of the blood vessel. The processor (e.g., the processor 120 of FIG. 1) may receive the electrical signal of the biometric sensor 370 to calculate heartbeat.

The details of the biometric sensor 370 will be described later.

Figure 5:
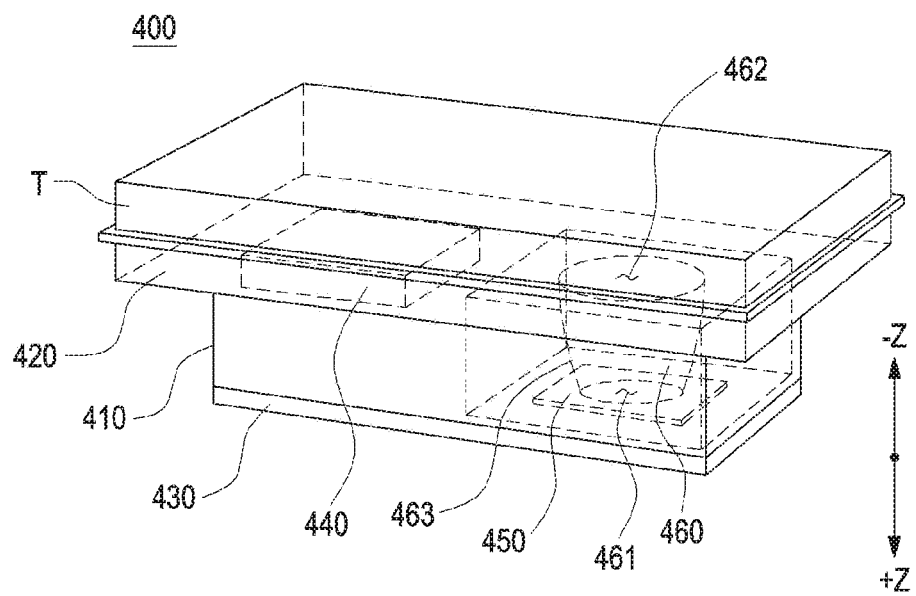
FIG. 5 illustrates a view of a biometric sensor module disposed in an electronic device according to various embodiments and a part of the user's body.

FIG. 5 illustrates a view of a biometric sensor module disposed in an electronic device according to various embodiments and a part of the user's body.

According to various embodiments, a biometric sensor module 400 may be accommodated in an electronic device (e.g., the electronic device 101 in FIG. 1 and the electronic device 300 in FIGS. 3 and 4). The biometric sensor module 400 may be disposed to face the rear face (e.g., the second direction (−Z axis direction)) of the electronic device 300. For example, the biometric sensor module 300 may be arranged to be in close contact with the second face 315 (e.g., the second face 315 in FIG. 3B) of the housing (e.g., the housing 310 in FIG. 3B), which comes into contact with the user's body, so that the biometric sensor module 300 is able to sense the user's vital reaction at a position as close to the user's body as possible.

According to various embodiments, the biometric sensor module 400 may include a circuit board 430, and the circuit board 430 may be electrically connected to the main circuit board of the electronic device 300 (e.g., the main circuit board 360 in FIG. 4). A shielding structure (not illustrated) may be disposed around the biometric sensor module 400 to shield other electronic components and/or the biometric sensor module 400 disposed on the circuit board 430.

Referring to FIG. 5, the biometric sensor module 400 may include a bracket 410, a cover glass 420 provided to cover one side of the bracket 410 and to face the outside (e.g., the second direction (−Z axis direction)), and a circuit board 430 disposed to face the other side (e.g., the first direction (+Z axis direction) and configured to mount electronic components thereon. As another example, the biometric sensor module 400 may include at least one light source 440 and light detector 450 disposed inside the bracket 410, and a light guide 460 disposed adjacent to the light source 440 or the light detector 450 so as to guide a light path.

According to various embodiments, the at least one light source 440 is mounted on the circuit board 430 and may transmit light in the second direction (−Z axis direction). The at least one light source 440 may emit light toward an external object (e.g., the user's body T), and the light detector 450 may receive light reflected from the external object. The at least one light source 440 and light detector 450 may be alternately arranged, and the at least one light source 440 and the light detector 450 may be disposed on the same plane. For example, the light detector 450 electrically connected to the circuit board 430 may be disposed on one face (e.g., the face oriented in the second direction (−Z axis direction)) of the circuit board 430, and a plurality of light sources 440 may be disposed at a distance apart from each other with the light detector 450 interposed therebetween. The plurality of light sources 440 may be disposed on the one face of the circuit board 430, and may be electrically connected to the circuit board 430.

According to various embodiments, the at least one light source 440 may emit light towards the cover glass 420. For example, the light source 440 may be an LED module or an LD module, and the light emitted from the light source 440 may exhibit various colors. The emitted light may have a wavelength range from about 300 nm to 1300 nm. As another example, the light emitted from the light source 440 may be green light and may have a wavelength in the range of about 510 nm to 550 nm. The light source 440 may be configured to cap the periphery of the circuit board in order to protect the circuit board that emits light, and a capping material may be, for example, epoxy. At least one pad (not illustrated) connected to the circuit board 430 may be disposed at the lower end of the light source 440 to be electrically connected to the circuit board 430.

According to various embodiments, the light detector 450 may be a photo diode or an image sensor. When the light emitted from the light source 440 is reflected from the user's body T, the light detector 450 may receive the reflected light and convert the light into current. For example, when a part of the light emitted from the light source 440 is reflected by the intravascular blood flow of the user and is returned to the light detector 450 in order to measure the user's heartbeat, the light detector 450 may convert the returned light into a current signal. As another example, since it is efficient to form the light detector 450 to have a large area in order to sufficiently receive the reflected light, the light detector 450 may be formed to be wider than an IC device disposed in the biometric sensor module.

According to various embodiments, the light detector 450 may be configured to cap the periphery of the circuit board 430 in order to protect the circuit board 430 that receives reflected light, and the capping material may be, for example, epoxy. At least one pad connected to the circuit board 430 may be disposed at the lower end of the light source 450 to be electrically connected to the circuit board 430.

According to an exemplary embodiment, the light detector 450 is disposed in parallel to the one light source 440. However, the disclosure is not limited thereto, and various numbers and arrangements of light sources and light detectors 450 may be provided so as to effectively receive the user's biometric information. For example, the light detector 450 may be disposed in parallel with or between the two light two light sources 440. As another example, a plurality of light sources 450 formed as a group may be disposed in an area, and a plurality of light detectors 450 may be at positions which are spaced apart from the center of the area by the same distance.

According to various embodiments, a light guide 460 for guiding a light path may be disposed on one side of the light source 440 or the light detector 450. Referring to FIG. 5, the light guide 460 may be disposed on the light detector 450 to guide light reflected from an external object. The light guide 460 is in the form of being opened on opposite sides, and may include a first hole 461 facing the light detector 450 and a second hole 462 facing the cover glass 420. The second hole 462 may be formed to have an area larger than that of the first hole 461. For example, the second hole 462 may be a circular hole having a diameter larger than that of the first hole 461. As another example, the light guide 460 includes a body 463 that forms a curved or inclined face from the second hole 462 toward the first hole 461, and the body 463 may be seamlessly bent in the first direction (+Z axis direction) and/or the second direction (−Z axis direction).

According to an embodiment, the first hole 461 of the light guide 460 may be disposed to face the light detector 450, and the second hole 462 may be disposed to face the cover glass 420. For example, the first hole 461 may be disposed to be in contact with or to be spaced apart from one face of the light detector 450, and the second hole 462 may be disposed to be in contact with or to be spaced apart from the cover glass 420. As another example, the light guide 460 may be manufactured such that the center of the first hole 461 and the center of the second hole 462 thereof are arranged on the same line. The light transmitted through the second hole 462 is reflected by the inner face of the body 463 of the light guide 460, and is filtered such that only a part of the light is provided to the light detector 450 through the first hole 461. According to an embodiment, the size of one surface of the light detector 450 that faces the first hole 461 is larger than the size of the first hole 461 of the light guide 460, but is not limited thereto. Various shapes of the light detector 450 may be provided to efficiently receive the user's biometric information. For example, the size of one surface of the light detector 450 may be smaller than that of the first hole 461.

The light guide 460 may include a compound parabolic collector (CPC) structure, and a detailed description thereof will be described later.

According to various embodiments, the bracket 410 is stacked on the circuit board 430, and may have a structure in which the light source 440 and/or the light detector 450 are opened in the second direction (−Z axis direction). As another example, the bracket 410 may include at least one partition (not illustrated) for preventing mutual signal interference between the light source 440 and the light detector 450.

According to various embodiments, the bracket 410 may have a plate shape including a plurality of openings, and the openings may be formed to penetrate the upper and lower faces of the bracket 410. The plurality of openings may include an opening for accommodating the light source 440 and an opening for accommodating the light detector 450 and the light guide 460, and respective openings may have different sizes. Through the openings, the light source 440 and the detector 450 may be connected to the circuit board 430 on one side and exposed in the second direction (−Z axis direction) on the other side.

According to various embodiments, the circuit board 430 may be disposed inside the biometric sensor module, and the light source 440 and/or the detector 450 may be disposed on the face of the circuit board 430 oriented in the second direction 450 (−Z axis direction). A controller is disposed on the circuit board 430 in the form of a chip to control the operation of the light source 440 and/or the light detector 450 by providing an electrical signal and may receive the signal of the light detector 450. The controller 431 may be connected to a processor (e.g., the processor 120 in FIG. 1) to control the intensity, driving channel, driving period, or the like of the light source 440.

According to various embodiments, the cover glass 420 may be disposed on one face of the bracket 410 oriented in the second direction (−Z axis direction). The cover glass 420 forms a part of the second face 315 to come into direct contact with the user's body, and may be made of a material that is capable of transmitting light as a substantially transparent plate.

Figure 6:
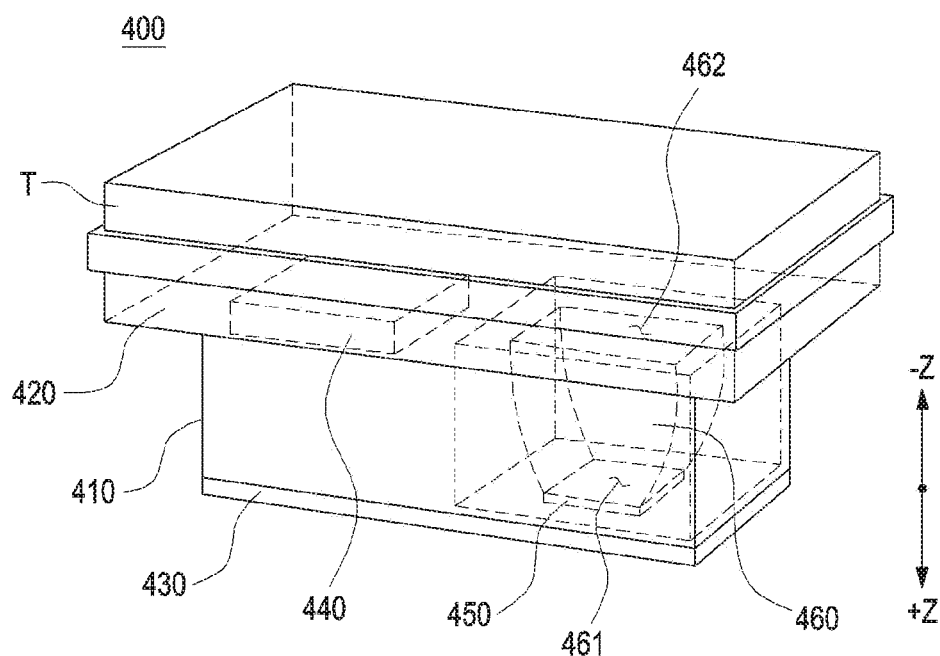
FIG. 6 illustrates a view of a biometric sensor module disposed in an electronic device according to another embodiment and a part of the user's body.

FIG. 6 illustrates a view of a biometric sensor module disposed in an electronic device according to another embodiment and a part of the user's body.

According to various embodiments, the biometric sensor module 400 may be accommodated in an electronic device (e.g., the electronic device 101 in FIG. 1 or the electronic device 300 in FIGS. 3 and 4). The circuit board 430 of the biometric sensor module 400 may be electrically connected to the main circuit board (e.g., the main circuit board 360 in FIG. 4). A shielding structure (not illustrated) may be disposed around the biometric sensor module 400 to shield other electronic components and/or the biometric sensor module 400 disposed on the circuit board 430.

Referring to FIG. 6, the biometric sensor module 400 may include a bracket 410, a cover glass 420 provided to cover one side of the bracket 410 and to face the outside, and a circuit board 430 disposed to face the other side of the bracket 410 and configured to mount electronic components thereon. As another example, the biometric sensor module 400 may include a light source 440 and a light detector 450 disposed inside the bracket 410, and a light guide 460 disposed adjacent to the light source 440 or the light detector 450 so as to guide a light path.

The structure of the bracket 410, the cover glass 420, the circuit board 430, the light source 440, and the light detector 450 of the biometric sensor module 400 of FIG. 6 may be the same as the structure of the bracket 410, the cover glass 420, the circuit board 430, the light source 440, and the light detector 450 of the biometric sensor module 400 of FIG. 5. Hereinafter, differences between light guides 460 will be mainly described.

According to various embodiments, the light guide 460 for guiding a light path may be disposed on one side of the light source 440 or the light detector 450. Referring to FIG. 6, the light guide 460 may be disposed on the light detector 450 to guide light reflected from an external object. The light guide 460 is in the form of being opened on opposite sides, and may include a first hole 461 facing the light detector 450 and a second hole 462 facing the cover glass 420. The second hole 462 may be formed to have an area larger than that of the first hole 461. For example, the second hole 462 may be a tetragonal hole having an area larger than that of the first hole 461. As another example, the light guide 460 may be seamlessly bent while forming a bent or inclined face facing from the second hole 462 to the first hole 461.

According to various embodiments, the first hole 461 and the second hole 462 of the light guide 460 may be formed in a tetragonal shape. For example, the first hole 461 may be formed in a rectangular shape corresponding to the shape of the light detector 450, and may cover the entire face of the light detector 450 that is oriented in the second direction (−Z axis direction). The second hole 462 may be formed in a shape corresponding to the first hole 461 to have an area larger than that of the first hole 461. As another example, the light guide 460 may be manufactured such that the center of the first hole 461 and the center of the second hole 462 thereof are arranged on the same line. The light transmitted through the second hole 462 is reflected from the inner face of the body 463 of the light guide 460, and is filtered such that only a part of the light is provided to the light detector 450 through the first hole 461. According to an embodiment, the size of the first hole 461 of the light guide 460 corresponds to the size of one face of the light detector 450 that faces the first hole 461, but is not limited thereto. The size of the light guide 460 may be varied depending on the restriction of the shape of the electronic device and the size of the biometric sensor module 400. Accordingly, the size of the first hole 461 may be designed to be larger or smaller than the size of the one face of the light detector 450. According to various embodiments, the biometric sensor module 400 of FIG. 5 and FIG. 6 may be disposed between the main circuit board 360 of the electronic device 300 (e.g., the main circuit board 360 in FIG. 5) and the second face 315 to sense the user's biometric information. The biometric sensor module 400 may be, for example, a sensor that collects or measures one or more biometric signals from the user. The biometric sensor module may collect raw data for measuring one or more of the user's blood pressure, blood flow, heart rate (HRM, HRV), body temperature, respiration rate, oxygen saturation, cardiac tone, blood sugar, waist size, height, weight, body fat, calorie consumption, brainwaves, voice, skin resistance, electromyogram, electrocardiogram, gait, ultrasound image, sleep state, facial expression (face), pupil dilation, or eye blink.

According to an embodiment, the electronic device may generate biometric information (or biometric characteristic information) by analyzing the biometric signals. For example, a pulse wave signal obtained through an HRV or HRM sensor may be a biometric signal. The electronic device may obtain primary biometric information such as an average heart rate or a heart rate distribution by analyzing the biometric signals, and may obtain secondary biometric information, such as a higher level of stress state or vascular aging degree, by processing the biometric information.

According to an embodiment, the biometric sensor module may simply output the collected user's biometric signals, and may output the biometric information by analyzing the biometric signals through a built-in processor. Accordingly, the biometric signals collected through the biometric sensor module may be transmitted to the processor within the biometric sensor module, the processor of the electronic device having the biometric sensor module embedded therein, or the processor of an external device (e.g., the server 108 or the electronic device 104 in FIG. 1), and may be used for generating biometric information. According to an embodiment, the user may use a portable phone having an ECG sensor embedded therein, or a wristwatch having a PPG sensor embedded therein.

When an electronic device (e.g., the electronic device 101 in FIG. 1) having the biometric sensor module embedded therein transmits a biometric signal to a remote device (e.g., the electronic device 104 of FIG. 1) or a server (e.g., the server 108 in FIG. 1) via a wired network, a wireless network, or a direct connection, the remote device or the server that receives the biometric signal may process the biometric signal to generate biometric information. According to an embodiment, when an electronic device (e.g., the electronic device 101 in FIG. 1) having the biometric sensor module embedded therein generates primary biometric information and transmits the generated biometric information to a remote device or a server, secondary biometric information may be generated in the remote device or the server. For example, the biometric signals collected by an HRM sensor or an HRV sensor embedded in a wristwatch device (an example of a wearable device) may be transmitted to a smartphone (an example of a host or main electronic device) wirelessly connected to the wristwatch device, and the smartphone may analyze the received biometric signals so as to generate biometric information. The biometric information may be transmitted using a wired or wireless communication scheme such that the biometric information is capable of being displayed on the display of the smart phone or capable of being displayed on the display of the wristwatch device. The biometric information may be displayed on or stored in, for example, at least one of the smartphone and the wristwatch device. According to an embodiment, the biometric signals collected by an HRM sensor or an HRV sensor embedded in an ear clip having an earphone function are transmitted to a wristwatch device or a smartphone, and the wristwatch device or the smartphone may generate biometric information. The generated biometric information may be delivered to one or more of other devices. When the biometric information is generated in the smartphone, the wristwatch device that receives the biometric information may display the biometric information on the display, and the ear clip that receives the biometric information may provide the biometric information to the user through sound.

According to an embodiment, as the heart repeats contraction and relaxation, the blood flow in a peripheral blood vessel changes, and the volume of the blood vessel changes. A photoplethysmography (PPG) sensor, which is a heartbeat sensor, is a sensor that measures the amount of light transmitted through an optical sensor and displays the heartbeat as a waveform. The PPG sensor is used to measure a change in the amount of blood in a blood vessel or an oxygen saturation. The PPG sensor is embedded in a clip, a wristwatch, a necklace, a band, a mobile phone, etc., and performs the measurement of a biological signal by attaching the heartbeat sensor to a body part (e.g., an ear, a wrist, a carotid artery, a finger, or an ankle) or by bringing the heartbeat sensor into contact with the body portion. As an example, in the case in which a measurement is performed using a finger, when the finger is brought into contact with a heartbeat sensor including a light source and a light detector and the contact is maintained for a predetermined time or longer, the heartbeat sensor measures a change reduced in the amount of light transmitted through the finger due to the increase of blood in the finger at the systole, and a change increased in the amount of light transmitted through the finger as the blood is released from the finger at the diastole.

The PPG may detect the amount of light as a voltage, and the PPG or the electronic device may convert the detected voltage into a digital value, thereby measuring the frequency of occurrence of the change. The heartbeat sensor or electronic device may determine how many pulses are generated per second based on the detected voltage, and may calculate a heart rate or an elapsed time between heartbeats based thereon. When the PPG sensor is embedded in a wristwatch, biomedical signals may be detected through the radial artery or the ulnar artery, and vital signals may be measured through a portion where blood vessels are distributed even if the blood vessels are not necessarily the arteries.

Depending on age, the heart rate per minute varies, and depending on the state of health and emotion, the heart rate pattern varies. An electronic device (e.g., the electronic device 101 in FIG. 1) may measure blood vessel elasticity through a pulse wave analysis, and may determine blood vessel age based on the blood vessel elasticity. That is, an electronic device may analyze the intensity of a heartbeat output, blood vessel elasticity, and a residual blood volume through the analysis of accelerated plethysmo graph (APG) obtained through the second differential of pulse wave signals. Through this, an auxiliary analysis, such as hypertension, diabetes, hyperlipidemia, arteriosclerosis, heart disease, peripheral blood circulation disorder may be performed by automatically analyzing a blood circulation state, such as blood vessel elasticity or vascular stiffness.

Figure 7:
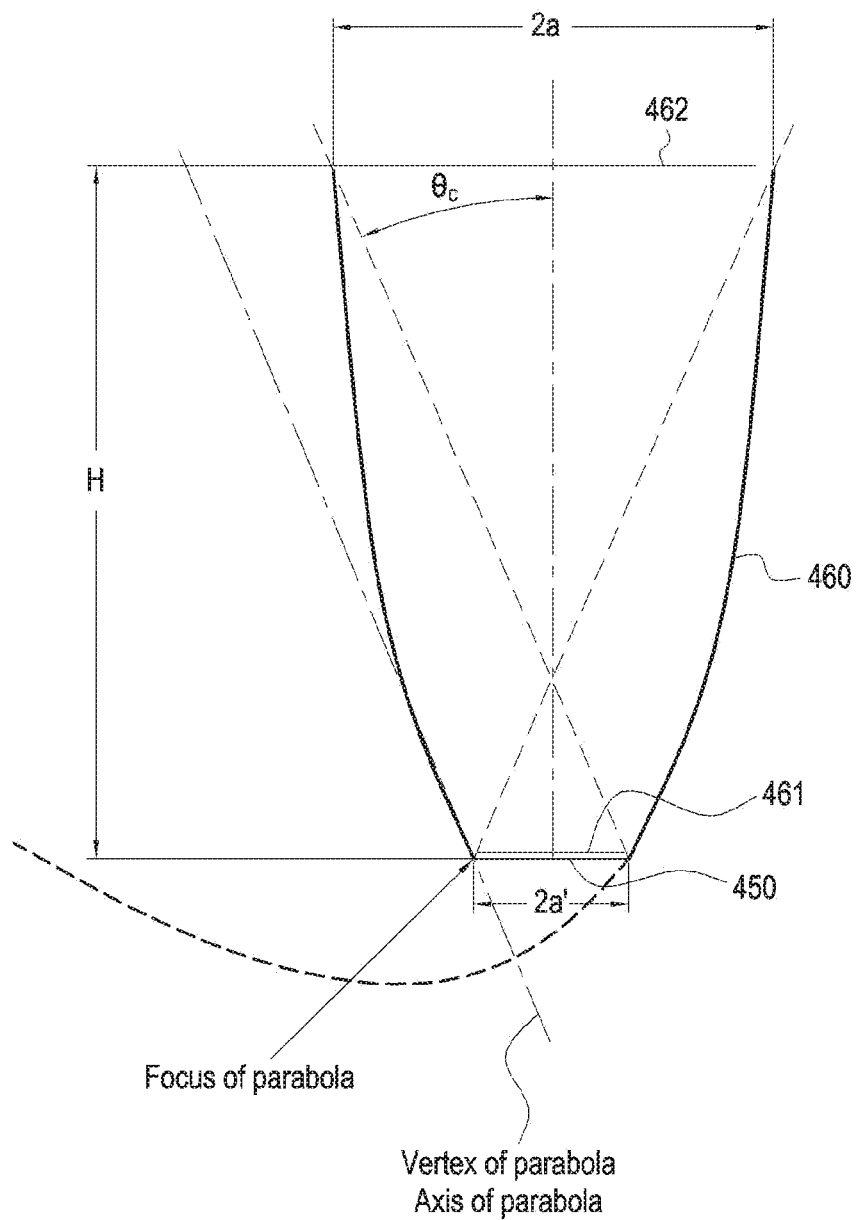
FIG. 7 illustrates a view of the configuration of a light guide according to various embodiments using mathematical expressions.
Figure 8A:
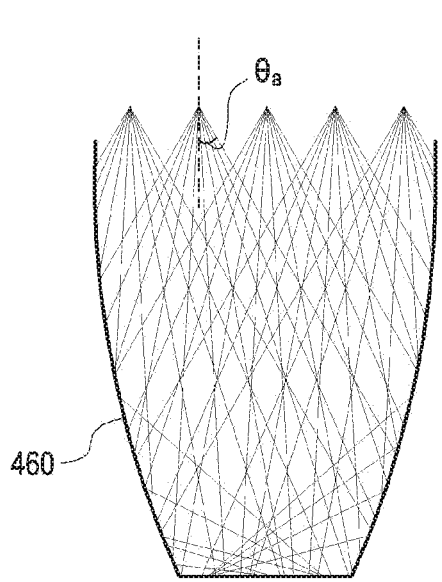
FIG. 8A illustrates a view exemplifying light beams that are capable of being incident on a light detector according to various embodiments depending on a critical angle.
Figure 8B:
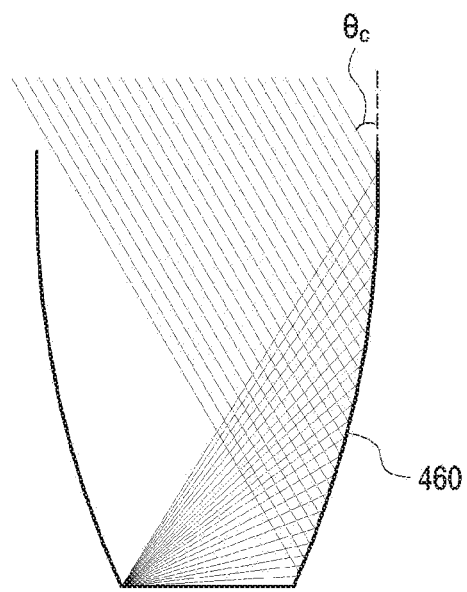
FIG. 8B illustrates a view exemplifying light beams that are capable of being incident on a light detector according to various embodiments depending on a critical angle.
Figure 8C:
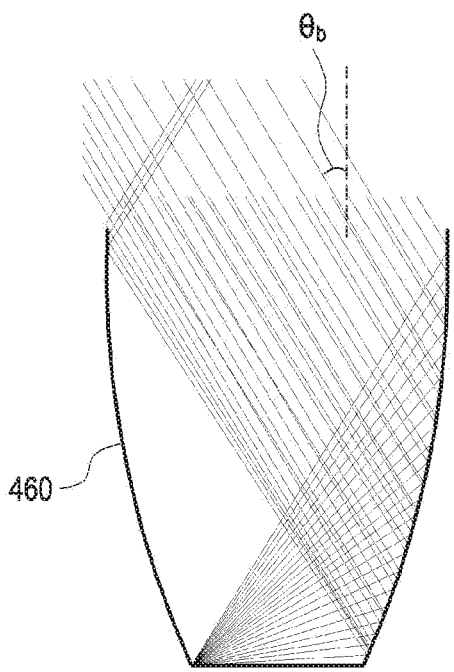
FIG. 8C illustrates a view exemplifying light beams that are capable of being incident on a light detector according to various embodiments depending on a critical angle.
Figure 8D:
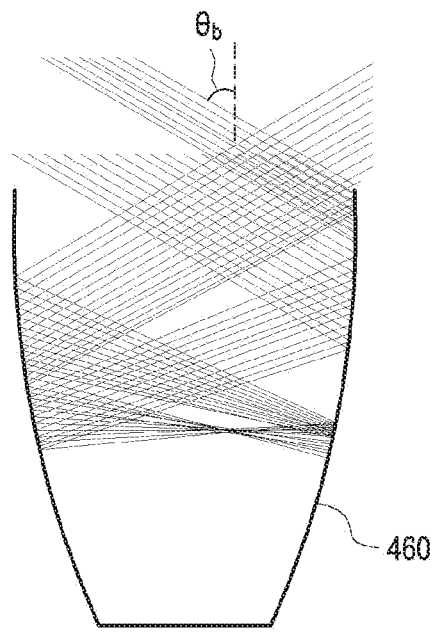
FIG. 8D illustrates a view exemplifying light beams that are capable of being incident on a light detector according to various embodiments depending on a critical angle.

FIG. 7 illustrates a view of the configuration of a light guide according to various embodiments using mathematical expressions. FIG. 8A illustrates a view exemplifying light beams that are capable of being incident on a light detector according to various embodiments depending on a critical angle. FIG. 8B illustrates a view exemplifying light beams that are capable of being incident on a light detector according to various embodiments depending on a critical angle. FIG. 8C illustrates a view exemplifying light beams that are capable of being incident on a light detector according to various embodiments depending on a critical angle. FIG. 8D illustrates a view exemplifying light beams that are capable of being incident on a light detector according to various embodiments depending on a critical angle.

According to various embodiments, a biometric sensor module (e.g., the biometric sensor module 400 in FIG. 5) disposed in an electronic device may include a light source (e.g., the light source 440 in FIG. 5), a light detector 450, a light guide 460, and a circuit board (e.g., the circuit board 430 of FIG. 5). The light guide 460 is disposed on the light source 440 and/or the light detector 450 to guide the path of light emitted from the light source 440 or to filter light incident on the light detector 450.

The structure of the light guide 460 and the light detector 450 of the biometric sensor module 400 in each of FIG. 7 and FIGS. 8A to 8D and may be partially or wholly the same as the structure of the light guide 460 and the light detector 450 of the biometric sensor module 400 in each of FIGS. 5 and 6.

Referring to FIG. 7, the light guide 460 may include a compound parabolic collector (CPC) structure. The light guide 460 may include a second hole 462 through which a part of the light reflected from an external object is received and a first hole 461 through which a part of the light entering the second hole 462 is capable of passing by being reflected. The light passing through the first hole 461 may enter the light detector 450.

According to various embodiments, the CPC structure of the light guide 460 is a filter for allowing only a part of the light incident to the inside to reach the light detector 450 and may have a tilted parabola shape in which one side of the surface thereof is tilted with respect to the opposite corner (focus of parabola). The shape of the parabola may be determined by Equations 1 to 3 as follows.

The tilt angle of the parabolic CPC structure may determine a predetermined critical angle $\theta_c$ at which light is capable of being incident on the light detector 450. For example, the incidence angle $\theta_c$ may be determined to a specific value by parameters that determine the size of the first hole 461 (or the size of the light source), the size of the second hole 462, and the height H of the CPC. As another example, the critical angle $\theta_c$ may have a value between 45 degrees and 80 degrees. When the curve characteristic of the parabola, the tilt angle, and the sizes of the first and second openings are determined depending on the structure of the formed light guide 460 by Equations 2 and 3 as follows, the light incident at an angle larger than the critical angle $\theta_c$ is all reflected and exits the CPC structure, and only the light incident at a critical angle $\theta_c$ or an angle smaller than the critical angle $\theta_c$ may be filtered to pass through the first hole 461 and to reach the light detector 450.

$$F = a'(1 + \sin \theta_c) \qquad \text{Equation 1}$$

$$a = a'/\sin \theta_c \qquad \text{Equation 2}$$

$$H = f \cos \theta_c / \sin^2 \theta_c \qquad \text{Equation 3}$$

In Equations 1 to 3, F is the focal distance of the parabola, a' is the radius of the first hole 461, a is the radius of the second hole 461, and $\theta_c$ is the critical angle.

Referring to FIGS. 8A to 8D, FIG. 8A shows that light beams having a first angle $\theta_a$ equal to or less than the critical angle $\theta_c$ are incident into the CPC structure and filtered light beams reach the surface of the light detector 450. FIG. 8B shows that light beams having the critical angle $\theta_c$ are incident into the CPC structure and filtered light beams reach the surface of the light detector 450. Unlike this, FIGS. 8C and 8D show that when light beams having a second angle $θ_b$ exceeding the critical angle $θ_c$ are incident into the CPC structure, the light beams are reflected from the inner surface and eventually exit the CPC structure.

Figure 9A:
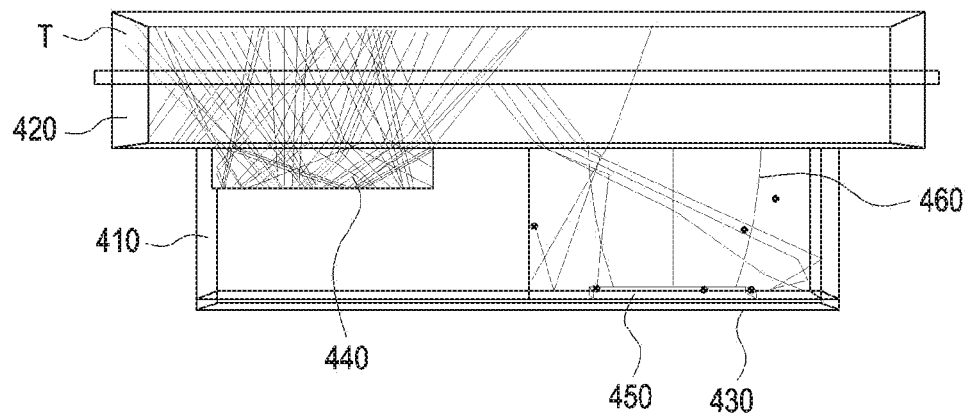
FIG. 9A illustrates a view of a simulation showing moving paths of light beams depending on the degree of separation between a biometric sensor module according to various embodiments and an external object.
Figure 9B:
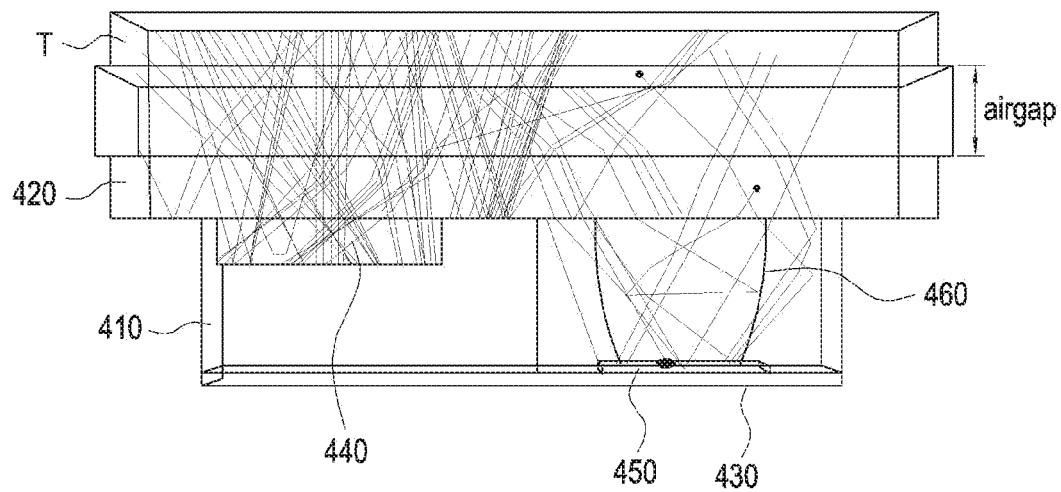
FIG. 9B illustrates a view of a simulation showing moving paths of light beams depending on the degree of separation between a biometric sensor module according to various embodiments and an external object.

FIG. 9A illustrates a view of a simulation showing moving paths of light beams depending on the degree of separation between a biometric sensor module according to various embodiments and an external object. FIG. 9B illustrates a view of a simulation showing moving paths of light beams depending on the degree of separation between a biometric sensor module according to various embodiments and an external object. FIGS. 9A and 9B show only a part of photons that progressed in the simulation.

FIGS. 9A and 9B are projection views each illustrating a biometric sensor module 400 disposed in an electronic device, the biometric sensor module 400 may include a bracket 410, a cover glass 420, a light source 440, a light detector 450, a light guide 460, and a circuit board 430. The light guide 460 is disposed on the light detector 450 to guide the path of light emitted from an external object or to filter light incident on the light detector 450.

The structure of the bracket 410, the cover glass 420, the light source 440, the light detector 450, the light guide 460, and the circuit board 430 of the biometric sensor module 400 in each of FIGS. 9A and 9B may be partially or wholly the same as the structure of the bracket 410, the cover glass 420, the light source 440, the light detector 450, the light guide 460, and the circuit board 430 of the biometric sensor module 400 in each of FIGS. 5 to 7.

FIG. 9A shows the state in which the cover glass 420 of the biometric sensor module 400 is disposed to be in contact with the user's skin T (e.g., the user's wrist). It can be seen that when the cover glass 420 and the user's skin T are completely in close contact with each other, the light directly directed to the light detector 450 without entering the skin T (noise) among the light provided from the light source 440 is all reflected by the light guide 460. Generally, when light emitted from the light source 440 does not enter the skin and is sensed by the light detector 450, the light is referred to as crosstalk noise. Because the noise is generated in a light component, it is necessary to design a sensor structure in which light does not reach the light source 450. The light guide 460 of the disclosure is capable of filtering out light incident at an angle other than the critical angle such that the crosstalk nose does not reach the light detector.

In FIG. 9A, the light, which does not enter the inside of the skin from the light source 440 but is directed to the light detector 450, does not enter the inside of the light guide 460 and is reflected from the outside to disappear. Even if the light enters the inside of the light guide 460, the light is not able to reach the light detector 450 and exits the light guide 460 to the outside.

FIG. 9B shows the state in which the cover glass 420 of the biometric sensor module 400 and the user's skin T (e.g., the user's wrist) are spaced from each other by a predetermined distance (an air gap). The cover glass 420 and the user's skin T are not always in contact with each other due to the movement of the user, and are frequently in the state of being spaced apart from each other by the predetermined distance. It can be seen that, even in the state in which the cover glass 420 and the user's skin T are spaced apart from each other by the predetermined distance (for example, about 0.5 mm to 2 mm), in the light provided from the light source 440, the light guide 460 reflects all the components of light that have an incident angle larger than the critical angle among the light beams, which are directly directed to the light detector 450 without entering the inside of the skin T.

In FIG. 9B, the light, which does not enter the inside of the skin from the light source 440 but is directed to the light detector 450, does not enter the inside of the light guide 460 and is reflected from the outside to disappear. Even if the light enters the inside of the light guide 460, the light is not able to reach the light detector 450 and exits the light guide 460 to the outside.

Figure 10A:
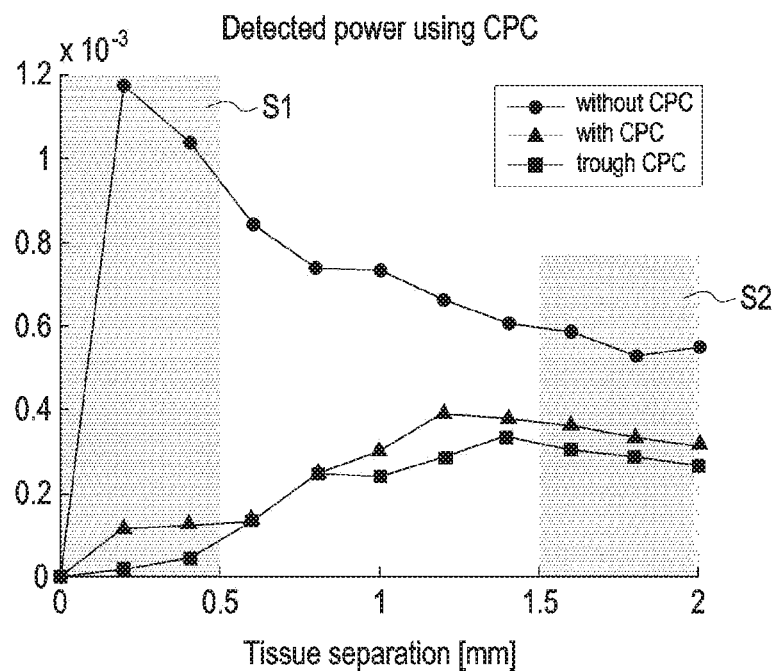
FIG. 10A illustrates a graph showing crosstalk noises before and after mounting a light guide according to various embodiments in comparison.
Figure 10B:
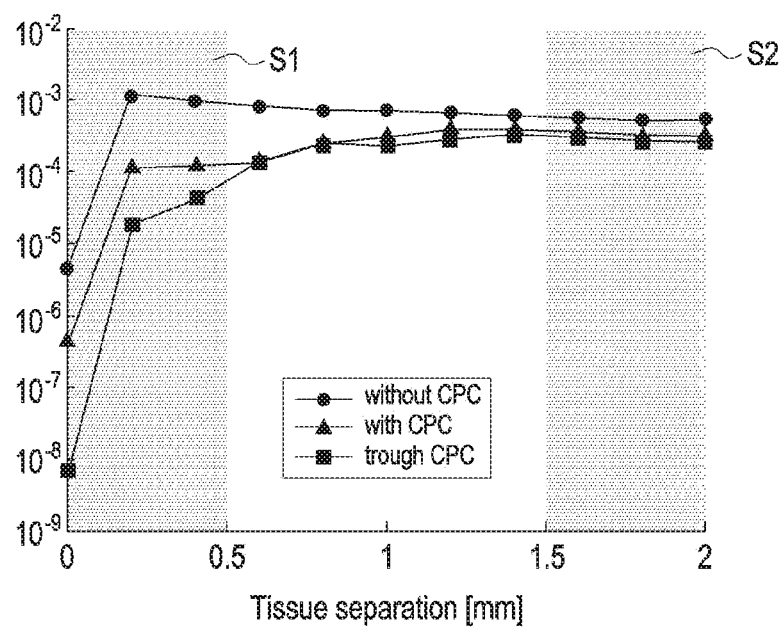
FIG. 10B is a graph showing crosstalk noises before and after mounting a light guide according to various embodiments in comparison.

FIG. 10A illustrates a graph showing crosstalk noises before and after mounting a light guide according to various embodiments in comparison. FIG. 10B illustrates a graph showing crosstalk noises before and after mounting a light guide according to various embodiments in comparison.

FIG. 10A illustrates a linear scale graph, and FIG. 10B illustrates a log scale graph.

In each of FIGS. 10A and 10B, the horizontal axis represents the separation distance between the biometric sensor module and the user's skin, and the vertical axis represents crosstalk noise. In FIGS. 10A and 10B, the line including circles represents a general biometric sensor module, which does not include a light guide, the line including triangles represents a biometric sensor module, which includes a light guide having the CPC structure of FIG. 5, and the line including squares represents a biometric sensor module, which includes a light guide having the CPC structure of FIG. 6.

According to various embodiments, it can be seen that crosstalk noise is reduced in all areas of the biometric sensor module, which includes the light guide of the disclosure compared with a biometric sensor module, which does not include a light guide. It can be seen that, from the state in which the biometric sensor module and the user's skin are in completely close contact with each other to the state in which the biometric sensor module and the user's skin are spaced apart from each other by 0.5 mm or less (S1), the biometric sensor module, which is provided with a light guide, does not generate crosstalk noise or generates a small amount of crosstalk noise compared with the biometric sensor module, which is not provided with a light guide. As another example, referring to FIG. 10B (log scale graph), in the state in which the biometric sensor module and the user's skin are in complete contact with each other, the biometric sensor module, which is provided with a light guide, is capable of reducing crosstalk noise about 10 to 100 times or more compared with the biometric sensor module, which is not provided with a light guide.

It can be seen that, when the separation distance between the biometric sensor module according to an embodiment and the user's skin gradually increases, crosstalk noise is generated, but the amount of crosstalk noise is small compared with the case the case in which the biometric sensor module, which is not provided with an optical guide, is used. For example, even in the case in which the separation distance is about 1.5 mm to 2 mm (S2), the biometric sensor module, which is provided with a light guide, reduces crosstalk noise about 50% or more compared with the biometric sensor module, which is not provided with a light guide.

Figure 11:
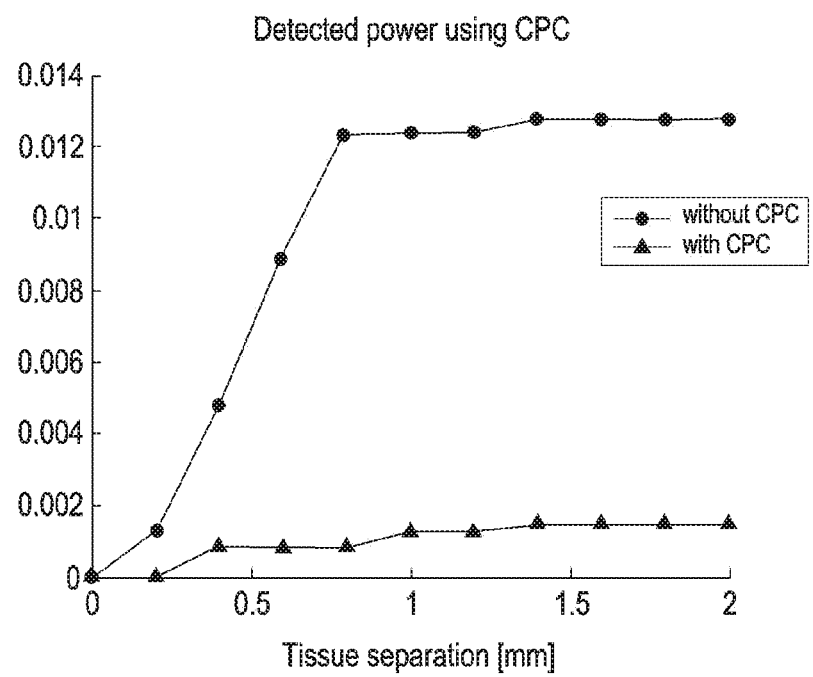
FIG. 11 illustrates a graph showing straight light noises before and after mounting a light guide according to various embodiments in comparison.

FIG. 11 illustrates a graph showing straight light noises before and after mounting a light guide according to various embodiments in comparison.

In FIG. 11, the horizontal axis represents the separation distance between the biometric sensor module and the user's skin, and the vertical axis represents stray light noise. In FIG. 11, the line including circles represents a general biometric sensor module, which does not include a light guide, and the line including triangles represents a biometric sensor module, which includes a light guide having the CPC structure of FIG. 5.

According to various embodiments, it can be seen that stray light noise is reduced in all areas of the biometric sensor module, which includes the light guide of the disclosure, compared with a biometric sensor module, which does not include a light guide. Generally, the stray light noise is a noise that is detected by a light detector when external light is introduced through an air gap existing when the biometric sensor module is in incomplete contact with the skin. For example, in the case of a biometric sensor module, which does not include a light guide, the external light introduced through the air gap may reach the light detector while maintaining the incident angle thereof. However, in the biometric sensor module, which includes a light guide, the external light may be filtered out and reflected to the outside if the critical angle is smaller than the incident angle of the external light.

Referring to FIG. 11, it can be seen that, even when a separation distance between the biometric sensor module and the user's skin occurs, the biometric sensor module, which includes a light guide, reduces the stray light noise about 10 times compared with the biometric sensor module, which does not include a light guide.

Figure 12:
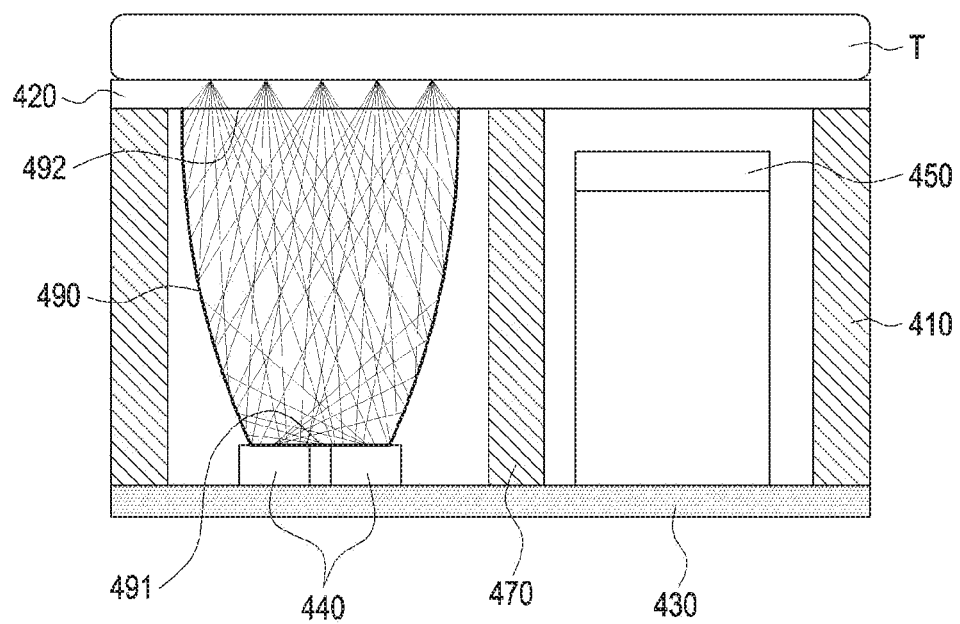
FIG. 12 illustrates a cross-sectional view of a biometric sensor module according to another embodiment disposed in an electronic device.

FIG. 12 illustrates a cross-sectional view illustrating a biometric sensor module according to another embodiment disposed in an electronic device.

According to various embodiments, a biometric sensor module 400 may be accommodated in an electronic device (e.g., the electronic device 101 in FIG. 1 and the electronic device 300 in FIGS. 3 and 4). A circuit board 430 of the biometric sensor module 400 may be electrically connected to a main circuit board (e.g., the main circuit board 360 in FIG. 4).

According to an embodiment, the biometric sensor module 400 may include a bracket 410, a cover glass 420 provided to cover one side of the bracket 410 and to face the outside, and a circuit board 430 disposed to face the other side of the bracket 410 and configured to mount electronic components thereon. As another example, the biometric sensor module 400 may include a partition wall 470 disposed inside the bracket 410, and a light guide 490 disposed adjacent to the light source 440 and the light detector 450, which is partitioned by the partition wall 470, so as to guide a light path.

The structure of the bracket 410, the cover glass 420, the circuit board 430, the light source 440, the light detector 450, and the light guide 490 of the biometric sensor module 400 of FIG. 12 may be the same as the structure of the bracket 410, the cover glass 420, the circuit board 430, the light source 440, the light detector 450, and the light guide 460 of the biometric sensor module 400 of FIG. 5. Hereinafter, differences between light guides 490 and 460 will be mainly described.

Figure 13:
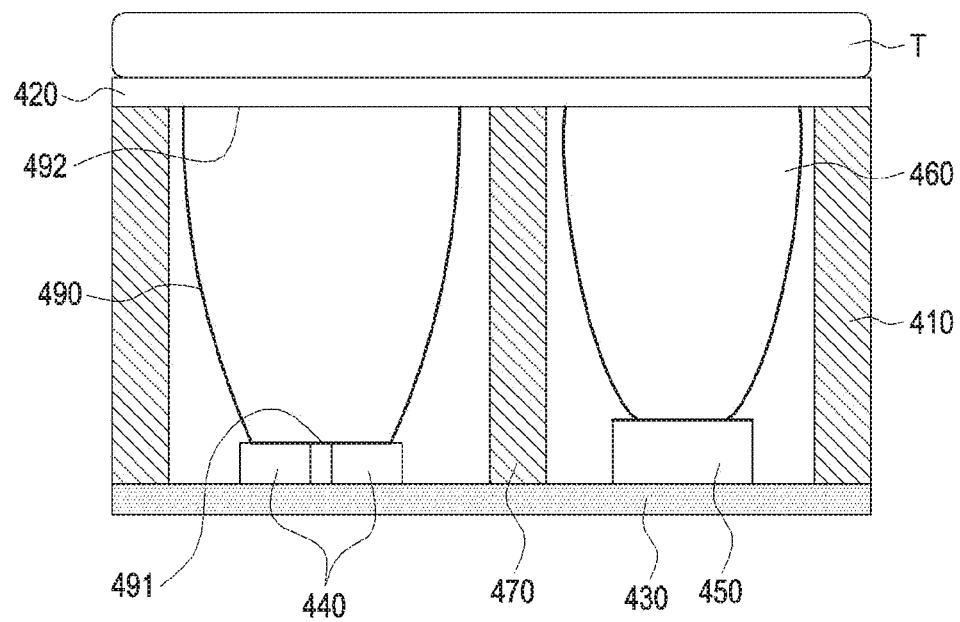
FIG. 13 illustrates a cross-sectional view of a biometric sensor module according to another embodiment disposed in an electronic device.

According to various embodiments, the light guide 490 for guiding a light path may be disposed on one side of the light source 440 and/or the light detector 450. Referring to FIG. 13, the light guide 490 may be disposed on the light detector 440 to filter light emitted from the light source 440. The light guide 490 is in the form of being opened on opposite sides, and may include a first hole 491 facing the light source 440 and a second hole 492 facing the cover glass 420. The second hole 492 may be formed to have an area larger than that of the first hole 491. For example, the second hole 492 may be a circular hole having a diameter larger than that of the first hole 491. As another example, the light guide 490 may be seamlessly bent while forming a bent or inclined face facing from the second hole 492 to the first hole 491.

According to various embodiments, the light guide 492 may be manufactured such that the center of the first hole 491 and the center of the second hole 492 thereof are arranged on the same line. The light guide 490 is capable of removing crosstalk noise by performing control such that, in the light emitted from the light source 440, the light reaching the inside of the user's skin only has an incident angle equal to or smaller than the critical angle and filtering out the light having an incident angle larger than the critical angle.

According to various embodiments, the biometric sensor module 400 may include a partition wall 470 that partitions the light source 440 and the light detector 450. The partition wall 470 may be formed at least one to prevent mutual signal interference between the light source 440 and the light detector 450.

FIG. 13 illustrates a cross-sectional view of a biometric sensor module according to another embodiment disposed in an electronic device.

According to various embodiments, a biometric sensor module 400 may be accommodated in an electronic device (e.g., the electronic device 101 in FIG. 1 and the electronic device 300 in FIGS. 3 and 4). A circuit board 430 of the biometric sensor module 400 may be electrically connected to a main circuit board (e.g., the main circuit board 360 in FIG. 4).

According to an embodiment, the biometric sensor module 400 may include a bracket 410, a cover glass 420 provided to cover one side of the bracket 410 and to face the outside, and a circuit board 430 disposed to face the other side of the bracket 410 and configured to mount electronic components thereon. As another example, the biometric sensor module 400 may include a light source 440 and a light detector 450 disposed inside the bracket 410, a first light guide 490 disposed adjacent to the light source 440 so as to guide a light path, and a second light guide 460 disposed adjacent to the light detector 450 to guide a light path. According to another embodiment, the biometric sensor module 400 may be disposed inside the bracket 410 to partition the light source 440 and the light detector 450.

The structure of the bracket 410, the cover glass 420, the circuit board 430, the light source 440, the light detector 450, and the second light guide 460 of the biometric sensor module 400 of FIG. 13 may be the same as the structure of the bracket 410, the cover glass 420, the circuit board 430, the light source 440, the light detector 450, and the light guide 460 of the biometric sensor module 400 of FIG. 5. The structure of the first light guide 490 and the partition wall 470 of the biometric sensor module 400 in FIG. 13 may be the same as the structure of the light guide 490 and the partition wall 470 of FIG. 12.

According to various embodiments, the first light guide 490 for guiding a light path may be disposed on one side of the light source 440. The second light guide 460 for guiding a light path may be disposed on one side of the light detector 450. The first light guide 490 may be disposed on the light source 440 to filter light emitted from the light source 440. For example, the first light guide 490 may remove crosstalk noise by filtering the light emitted from the light source 440 such that the incident angle for reaching the user's skin becomes an angle smaller than the critical angle. As another example, the second light guide 460 may be disposed on the light detector 450 to guide light reflected from an external object. The shapes of the first light guide 490 and the second light guide may be the same as those illustrated in FIG. 7 and FIGS. 8A to 8D.

Figure 14:
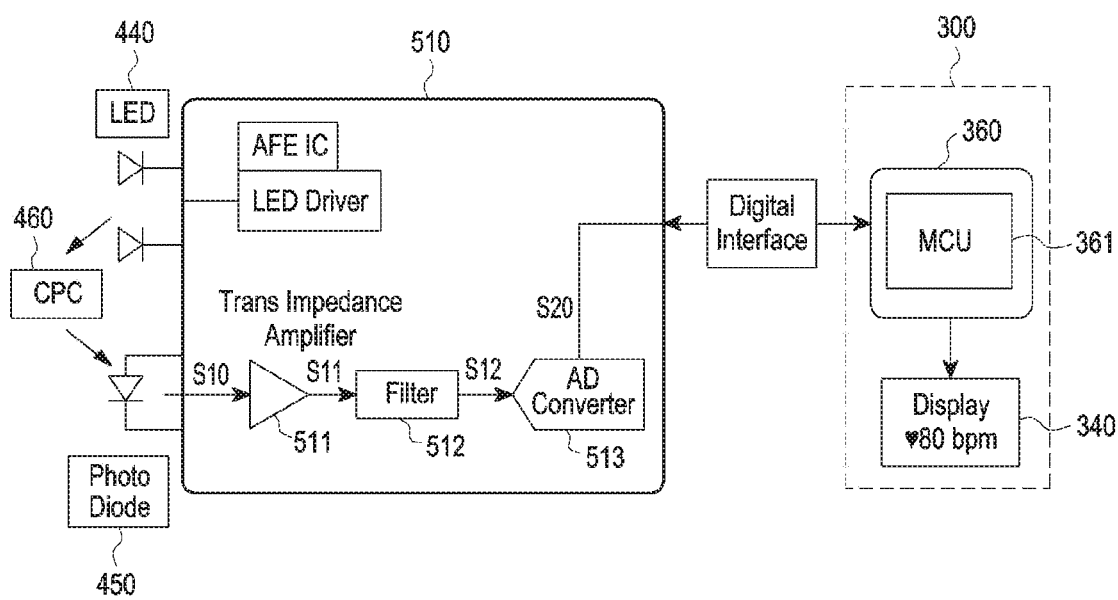
FIG. 14 illustrates a circuit diagram for explaining the operation of a biometric sensor module according to various embodiments.
Figure 15:
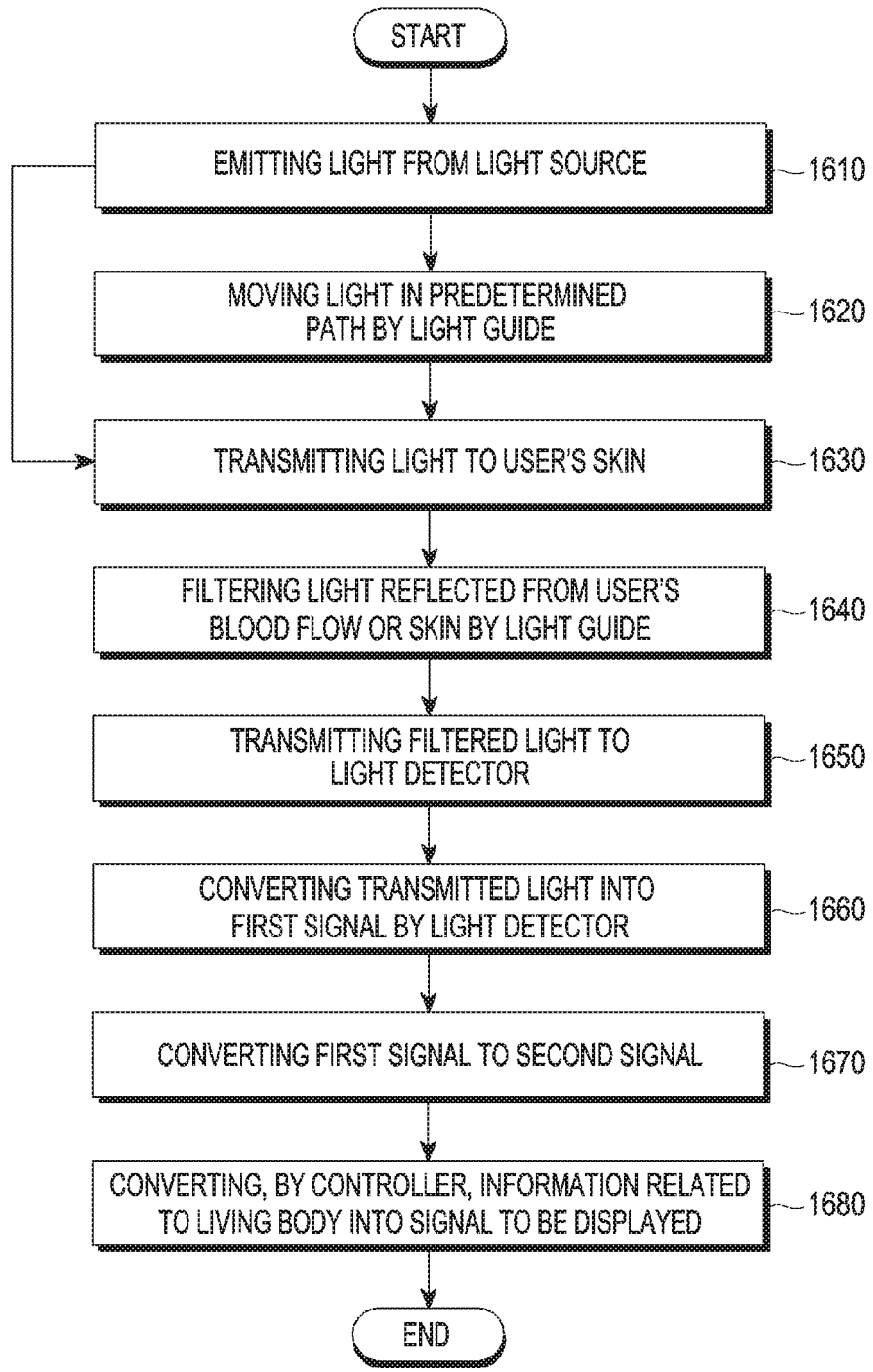
FIG. 15 illustrates a flowchart for explaining the operation of a biometric sensor module.

FIG. 14 illustrates a circuit diagram for explaining the operation of a biometric sensor module according to various embodiments. FIG. 15 is a flowchart for explaining the operation of a biometric sensor module.

Referring to FIGS. 14 and 15, an electronic device 300 (e.g., the electronic device 101 in FIG. 1) according to various embodiments may include a biometric sensor module 400. A circuit board (e.g., the circuit board 430 in FIG. 5) of the biometric sensor module 400 may be electrically connected to the main circuit board 360.

According to an embodiment, the biometric sensor module 400 may include a bracket (e.g., the bracket 410 in FIG. 5), a cover glass (e.g., the cover glass 420 in FIG. 5) provided to cover one side of the bracket 410 and to face the outside, and a circuit board (e.g., the circuit board 430 in FIG. 5) disposed to face the other side of the bracket 410 and configured to mount electronic components thereon. As another example, the biometric sensor module 400 may include a light source 440 and a light detector 450 disposed inside the bracket 410, a light guide 460 disposed adjacent to the light source 440 or the light detector 450 so as to guide a light path, and an IC device 510.

According to various embodiments, the electronic device 300 may be a smart watch and may be used to determine the user's heartbeat using the intravascular blood flow inside the user's wrist.

According to various embodiments, the light may be emitted from the light source 440 disposed on the circuit board 430 to be oriented in the second direction (−Z axis direction) (1610). The emitted light may be transmitted to an intravascular blood flow in an inner skin layer of a user through a first light path (1630). For example, at least a part of the light emitted from the light source 440 may be absorbed in and/or reflected from the intravascular blood flow. The light source 440 may be an LED, and may use green light that can be efficiently transmitted to the bloodstream inside the user's wrist. The light guide 460 disposed on one side of the light emitting unit 440 is provided in a CPC structure to enhance the rectilinear advancement property in a light traveling direction (1620). However, the light guide 460 may be omitted depending on whether to be disposed on the light source 440 or not.

According to various embodiments, the light reflected from the blood flow may be filtered 1640 through the light guide 460 disposed on one side of the light detector 450 through a second light path (1640). A part of the filtered light may then be transmitted to the light detector 450 disposed on the circuit board 430 in the second direction (−Z axis direction) (1650). As another example, according to an embodiment, the light detector 450 may be disposed on the same plane as the light source 440. The biometric sensor module 400 may include a partition wall (not illustrated) disposed between the light source 440 and the light detector 450 to prevent the light directly emitted from the light source 440 from being interfered with.

According to various embodiments, when a part of the reflected light is received by the light detector 450 along the second light path, the light detector 450 may convert the reflected light into a first signal S10 (1660). The converted first signal may be transmitted to the IC device 510. According to one embodiment, the first signal may be a current signal.

According to various embodiments, the IC device 510 may convert the first signal S10 received from the light detector 450 into a second signal S20, and may then transmit the second signal S20 to a controller 361 on the main circuit board 360 of the electronic device via a digital interface, such as an I2C or an SPI (1670). According to an embodiment, the IC device 510 may include a plurality of processing units, of which the first processing unit 511 may perform the operation of converting and amplifying the first signal S10 received from the right detector (e.g., a photodiode) into a $(1-a)_{th}$ signal S11. For example, the first processing unit 511 may be a transimpedance amplifier, and the $(1-a)_{th}$ signal S11 may be a voltage signal.

According to various embodiments, the $(1-a)_{th}$ signal S11 converted by the first processing unit 511 of the IC device 510 may be output as a $(1-b)_{th}$ signal S12 form which noise has been removed through a second processing unit 512. For example, the second processing unit 512 may be a low-pass filter (LPF), and may extract the $(1-b)_{th}$ signal, from which signal noise of a high frequency band has been removed by the second processing unit 512.

According to various embodiments, the $(1-b)_{th}$ signal, which has been processed by the second processing unit 512, may be quantized by a third processing unit 513, and the quantized second signal S20 may be transmitted to the main circuit board 360 of the electronic device 300 through a communication method using an I2C protocol and/or an SPI protocol. For example, the third processing unit 513 may be an analog to digital (AD) converter.

According to various embodiments, the processing signal transmitted from the third processing unit 513 may be transmitted, as a signal capable of being easily recognized by the user (e.g., a heart rate-related signal, a stress-related signal, a blood pressure-related signal, or an SpO2-related signal) to the display 340 through the execution of a preset algorithm by the controller 361 in the circuit board (1680). The display 340 may display the heart rate-related signal to the outside, thereby providing information to the user. For example, the controller 361 may be a micro controller unit (MCU). The display 340 may be disposed to be oriented in the first direction (the direction opposite the wrist), so that the user is capable of conveniently checking biometric information related to the user's own heart rate.

An electronic device (e.g., the electronic device 300 in FIGS. 3 and 4) according to various embodiments may include: a housing (e.g., the housing 310 in FIG. 3) including a front plate (e.g., the first face 313 in FIG. 3) oriented in a first direction (e.g., the first direction (+Z axis direction) in FIG. 4) and a rear plate (e.g., the second face 315 in FIG. 3) oriented in a second direction (the second direction (−Z axis direction) in FIG. 4), which is opposite the first direction; a display (e.g., the display 340 in FIG. 4) visible through at least a portion of the front plate; and a biometric sensor module (e.g., the biometric sensor 370 in FIG. 4 or the biometric sensor module 400 in FIG. 5) located between the front plate and the rear plate, the biometric sensor module being exposed through at least a portion of the rear plate. The biometric sensor module may include: a cover glass (e.g., the cover glass 420 in FIG. 5) oriented in the second direction; at least one light source (e.g., the light source 440 in FIG. 5) configured to emit light to the outside; a light detector (e.g., the light detector 450 in FIG. 5) disposed to adjacent to the at least one light source, and configured to receive reflected light corresponding to light emitted from the light source; a light guide (e.g., the light guide 460 in FIG. 5) disposed between the light detector and the cover glass, and configured to provide a path of the reflected light received by the light detector; and a circuit board (e.g., the circuit board 430 in FIG. 5) electrically connected to the at least one light source and the light detector.

According to various embodiments, the light guide is disposed on the light detector and may filter out the reflected light incident at an angle equal to or larger than a predetermined angle with respect to the second direction.

According to various embodiments, the light guide may include a first hole (e.g., the first hole 461 in FIG. 5) facing the light detector, and a second hole (e.g., the second hole 462 in FIG. 5) disposed to face the cover glass and having a size larger than that of the first hole.

According to various embodiments, the light guide may have a curved body (e.g., the body 463 in FIG. 5) having a shape curved from the second hole to the first hole, and the center of the second hole and the center of the first hole may be arranged on the same line.

According to various embodiments, the biometric sensor module may measure a change in a flow rate of blood flowing in a blood vessel of a user, and may detect a heartbeat signal based on at least a part of the measured change.

According to various embodiments, the light detector may be disposed on the same plane as the at least one light source, and may include a photo diode configured to receive the reflected light and to convert the received light into a first signal.

According to various embodiments, the electronic device may further include an IC device (e.g., the IC device 510 in FIG. 15) configured to convert the first signal provided from the light detector into a second signal, and to provide the second signal to a main circuit board (e.g., the main circuit board 360 in FIG. 4) disposed in the electronic device.

According to various embodiments, the light guide may have a compound parabolic collector (CPC) structure including opposite opened ends and having a parabola shape.

According to various embodiments, the biometric sensor module may further include a bracket (e.g., the bracket 410 in FIG. 5) configured to accommodate at least a part of the light source and the light detector, the bracket including at least one opening such that the light source or the light detector is exposed to the outside of the biometric sensor module.

According to various embodiments, the cover glass may be formed on at least a portion of the rear plate as a transparent plate and may be disposed to face a main circuit disposed inside the housing with the circuit board interposed therebetween. The circuit board and the main circuit board may be electrically connected to each other.

According to various embodiments, the IC device may include a plurality of processing units. The IC device may include a first processing unit (e.g., the first processing unit 511 in FIG. 15) configured to convert the first signal (e.g., the first signal S10 in FIG. 15) transmitted from the light detector into a $(1\text{-}a)^{th}$ signal (e.g., the $(1\text{-}a)^{th}$ signal S11 in FIG. 15) and to amplify the $(1\text{-}a)^{th}$ signal, a second processing unit (e.g., the second processing unit 512 in FIG. 15) configured to remove noise from the $(1\text{-}a)^{th}$ signal of the first processing unit to output a $(1\text{-}b)^{th}$ signal (e.g., the $(1\text{-}b)^{th}$ signal in FIG. 15), and a third processing unit (e.g., the third processing unit 513 in FIG. 15) configured to provide the second signal (e.g., the second signal S20 in FIG. 15) obtained by quantizing the $(1\text{-}b)^{th}$ signal of the second processing unit to the main circuit board.

According to various embodiments, the main circuit board may include a controller (e.g., the controller 361 in FIG. 15) configured to output the second signal transmitted from the IC device as a user's heart rate signal by executing a predetermined algorithm, and to provide the heart rate signal to be displayed on the display.

According to various embodiments, the light guide may include a first hole facing the light detector, and a second hole disposed to face the cover glass and having a size different from that of the first hole, and the first hole may be formed to have a size and shape corresponding to one face of the light detector that is oriented in the second direction.

According to various embodiments, the light emitted from the light source may be reflected from a blood flow of the user to be provided to the light detector. The biometric sensor module may further include a partition located between the light source and the light detector to prevent light other than the reflected light from being provided to the light detector.

According to various embodiments, the biometric sensor module may further include another light guide disposed between the light source and the cover glass and configured to provide a predetermined path of the light emitted from the light source.

A biometric sensor module according to various embodiments may include: a cover glass exposed to the outside; at least one light source configured to emit light to the outside; a light detector disposed to adjacent to the at least one light source, and configured to receive reflected light corresponding to light emitted from the light source; a first light guide disposed between the light source and the cover glass, and configured to provide a path of the light emitted from the light source; a second light guide disposed between the light detector and the cover glass, and configured to provide a path of the reflected light received by the light detector; and a circuit board electrically connected to the at least one light source and the light detector.

According to various embodiments, a center of the second light guide and a center of the light detector may be arranged on a same line, and the second light guide may filter out the reflected light incident at an angle equal to or larger than a predetermined angle with respect to the same line.

According to various embodiments, the second light guide may include a first hole facing the light detector, a second hole disposed to face the cover glass and having a size larger than that of the first hole, and a curved body curved from the second hole to the first hole. The predetermined angle may range from 45 degrees to 80 degrees.

An electronic device according to various embodiments may include: a housing including a front plate oriented in a first direction and a rear plate oriented in a second direction, which is opposite the first direction; a display visible through at least a portion of the front plate; and a biometric sensor module located between the front plate and the rear plate, the biometric sensor module being exposed through the rear plate. The biometric sensor module may include: a cover glass (e.g., the cover glass 420 in FIG. 6) oriented in the second direction; at least one light source (e.g., the light source 440 in FIG. 6) configured to emit light to the outside; a light detector (e.g., the light detector 450 in FIG. 6) disposed to adjacent to the at least one light source, and configured to receive reflected light corresponding to light emitted from the light source; a light guide (e.g., the light guide 460 in FIG. 6) disposed between the light detector and the cover glass, and configured to provide a predetermined path of the light emitted from the light source; and a circuit board (e.g., the circuit board 430 in FIG. 6) electrically connected to the at least one light source and the light detector.

According to various embodiments, the light guide may include a first hole facing the light source and a second hole disposed to face the cover glass and having a size larger than that of the first hole.

While the disclosure has been shown and described with reference to certain embodiments thereof, it will be understood by those skilled in the art that various changes in form and details may be made therein without departing from the spirit and scope of the disclosure as defined by the appended claims.

Although the present disclosure has been described with various embodiments, various changes and modifications may be suggested to one skilled in the art. It is intended that the present disclosure encompass such changes and modifications as fall within the scope of the appended claims

What is claimed is:

1. An electronic device comprising:
a housing including a front plate oriented in a first direction and a rear plate oriented in a second direction, that is opposite to the first direction;
a display visible through at least a portion of the front plate; and
a biometric sensor module located between the front plate and the rear plate, the biometric sensor module exposed through at least a portion of the rear plate,
wherein the biometric sensor module includes:
a cover glass oriented in the second direction;
at least one light source configured to emit light to an outside of the biometric sensor module;
a light detector disposed adjacent to the at least one light source, and configured to receive reflected light corresponding to light emitted from the light source;
a light guide disposed between the light detector and the cover glass, and configured to provide a path of the reflected light received by the light detector, wherein the light guide has opposite opened ends and includes a compound parabolic collector (CPC) structure having a parabola shape; and
a circuit board electrically connected to the at least one light source and the light detector,
wherein the light guide is disposed on the light detector, and is configured to filter out the reflected light incident at an angle equal to or larger than a predetermined angle with respect to the second direction,
wherein the light detector is disposed on a same plane as the at least one light source, and includes a photo diode configured to receive the reflected light and to convert the received light into a first signal,
wherein the electronic device further comprises an integrated circuit (IC) device configured to convert the first signal provided from the light detector into a second signal, and to provide the second signal to a main circuit board disposed in the electronic device, and
wherein the IC device includes a plurality of processing units including:
a first processing unit configured to convert the first signal transmitted from the light detector into a third signal and to amplify the third signal;
a second processing unit configured to remove noise from the third signal of the first processing unit to output a fourth signal; and
a third processing unit configured to provide a second signal obtained by quantizing the fourth signal of the second processing unit to the main circuit board.

2. The electronic device of claim 1, wherein the light guide includes:
a first hole facing the light detector, and
a second hole disposed to face the cover glass and having a size larger than that of the first hole.

3. The electronic device of claim 2, wherein:
the light guide includes a curved body having a shape curved from the second hole to the first hole, and
the second hole and the first hole are arranged on a same line.

4. The electronic device of claim 1, wherein the biometric sensor module is configured to:
measure a change in a flow rate of blood flowing in a blood vessel of a user, and
detect a heartbeat signal based on at least a part of the measured change.

5. The electronic device of claim 1, wherein the biometric sensor module further includes a bracket configured to accommodate at least a part of the light source and the light detector, the bracket including at least one opening such that the light source or the light detector is exposed to the outside of the biometric sensor module.

6. The electronic device of claim 1, wherein:
the cover glass is formed on at least a portion of the rear plate as a transparent plate, and is disposed to face the main circuit board disposed inside the housing with the circuit board interposed therebetween, and
the circuit board and the main circuit board are electrically connected to each other.

7. The electronic device of claim 1, wherein the main circuit board includes a controller configured to:
output the second signal transmitted from the IC device as a heart rate signal of a user by executing a predetermined algorithm, and
to provide the heart rate signal to be displayed on the display.

8. The electronic device of claim 1, wherein:
the light guide includes:
a first hole facing the light detector, and
a second hole disposed to face the cover glass and having a size different from that of the first hole, and
the first hole is formed to have a size and shape corresponding to one face of the light detector that is oriented in the second direction.

9. The electronic device of claim 2, wherein:
the light emitted from the light source is reflected from a blood flow of a user to be provided to the light detector, and
the biometric sensor module further includes a partition located between the light source and the light detector to prevent exposure of light other than the reflected light to the light detector.

10. The electronic device of claim 2, wherein the biometric sensor module further includes another light guide disposed between the light source and the cover glass and configured to provide a predetermined path of the light emitted from the light source.

11. A biometric sensor module comprising:
a cover glass exposed to an outside of the biometric sensor module;
at least one light source configured to emit light to the outside of the biometric sensor module;
a light detector disposed adjacent to the at least one light source, and configured to receive reflected light corresponding to light emitted from the light source;
a first light guide disposed between the light source and the cover glass, and configured to provide a path of the light emitted from the light source;
a second light guide disposed between the light detector and the cover glass, and configured to provide a path of the reflected light received by the light detector, wherein the first light guide has opposite opened ends and includes a compound parabolic collector (CPC) structure having a parabola shape; and a circuit board electrically connected to the at least one light source and the light detector, wherein a center of the second light guide and a center of the light detector are arranged on a same line, and, and the second light guide is configured to filter out the reflected light incident at an angle equal to or larger than a predetermined angle with respect to the same line, wherein the light detector is disposed on a same plane as the at least one light source, and includes a photo diode configured to receive the reflected light and to convert the received light into a first signal, wherein the biometric sensor module further comprises an integrated circuit (IC) device configured to convert the first signal provided from the light detector into a second signal, and to provide the second signal to a main circuit board disposed in the biometric sensor module, and wherein the IC device includes a plurality of processing units including:
   a first processing unit configured to convert the first signal transmitted from the light detector into a third signal and to amplify the third signal;
   a second processing unit configured to remove noise from the third signal of the first processing unit to output a fourth signal; and a third processing unit configured to provide a second signal obtained by quantizing the fourth signal of the second processing unit to the main circuit board.

12. The biometric sensor module of claim 11, wherein:
the second light guide includes:
   a first hole facing the light detector;
   a second hole disposed to face the cover glass and having a size larger than that of the first hole; and
   a curved body curved from the second hole to the first hole, and
the predetermined angle ranges from 45 degrees to 80 degrees.

13. An electronic device comprising:
a housing including a front plate oriented in a first direction and a rear plate oriented in a second direction, that is opposite the first direction;
a display visible through at least a portion of the front plate; and
a biometric sensor module located between the front plate and the rear plate, the biometric sensor module exposed through at least a portion of the rear plate,
wherein the biometric sensor module includes:
   a cover glass oriented in the second direction;
   at least one light source configured to emit light to an outside of the biometric sensor module;
   a light detector disposed adjacent to the at least one light source, and configured to receive reflected light corresponding to light emitted from the light source;
   a first light guide disposed between the light source and the cover glass, and configured to provide a path of the light emitted from the light source, wherein the first light guide has opposite opened ends and includes a compound parabolic collector (CPC) structure having a parabola shape;
   a second light guide disposed on the light detector, and is configured to filter out the reflected light incident at an angle equal to or larger than a predetermined angle with respect to the second direction; and
a circuit board electrically connected to the at least one light source and the light detector,
wherein the light detector is disposed on a same plane as the at least one light source, and includes a photo diode configured to receive the reflected light and to convert the received light into a first signal,
wherein the electronic device further comprises an integrated circuit (IC) device configured to convert the first signal provided from the light detector into a second signal, and to provide the second signal to a main circuit board disposed in the electronic device, and
wherein the IC device includes a plurality of processing units including:
   a first processing unit configured to convert the first signal transmitted from the light detector into a third signal and to amplify the third signal;
   a second processing unit configured to remove noise from the third signal of the first processing unit to output a fourth signal; and
a third processing unit configured to provide a second signal obtained by quantizing the fourth signal of the second processing unit to the main circuit board.

14. The electronic device of claim 13, further comprising:
a second light guide disposed between the light detector and the cover glass, and configured to provide a path of the reflected light received by the light detector,
wherein the second light guide has opposite opened ends and includes a CPC structure having a parabola shape.

* * * * *